US012397050B2

(12) United States Patent
Verhoeven et al.

(10) Patent No.: US 12,397,050 B2
(45) Date of Patent: *Aug. 26, 2025

(54) UNIVERSAL MAMMALIAN INFLUENZA VACCINE

(71) Applicant: Iowa State University Research Foundation, Inc., Ames, IA (US)

(72) Inventors: David Verhoeven, Ames, IA (US); Jessie Dorothy Trujillo, Manhattan, KS (US); Brett Sponseller, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/296,150

(22) Filed: Apr. 5, 2023

(65) Prior Publication Data

US 2023/0372466 A1 Nov. 23, 2023

Related U.S. Application Data

(63) Continuation of application No. 16/400,817, filed on May 1, 2019, now Pat. No. 11,672,852, which is a continuation-in-part of application No. PCT/US2017/059647, filed on Nov. 2, 2017.

(60) Provisional application No. 62/416,466, filed on Nov. 2, 2016.

(51) Int. Cl.
*A61K 39/145* (2006.01)
*A61P 31/16* (2006.01)
*C07K 14/005* (2006.01)
*C12N 7/00* (2006.01)
*A61K 39/00* (2006.01)

(52) U.S. Cl.
CPC ............ *A61K 39/145* (2013.01); *A61P 31/16* (2018.01); *C07K 14/005* (2013.01); *C12N 7/00* (2013.01); *A61K 2039/515* (2013.01); *A61K 2039/52* (2013.01); *A61K 2039/5252* (2013.01); *A61K 2039/5254* (2013.01); *A61K 2039/5258* (2013.01); *A61K 2039/552* (2013.01); *A61K 2039/55505* (2013.01); *A61K 2039/70* (2013.01); *C12N 2760/16122* (2013.01); *C12N 2760/16134* (2013.01); *C12N 2760/16171* (2013.01)

(58) Field of Classification Search
None
See application file for complete search history.

(56) References Cited

U.S. PATENT DOCUMENTS

| 8,506,967 B2 * | 8/2013 | Smith .................. A61K 39/145 424/210.1 |
| 9,492,530 B2 * | 11/2016 | Olsen .................. A61K 9/0043 |
| 2015/0132330 A1 | 5/2015 | Garcia-Sastre et al. |
| 2016/0051662 A1 | 2/2016 | Olsen et al. |

FOREIGN PATENT DOCUMENTS

WO 2015195218 A1 12/2015

OTHER PUBLICATIONS

Chen et al. PNAS, 2014, vol. 111, p. 2476-2481).*
Wang et al., "Broadly Protective Monoclonal Antibodies against H3 Influenza Viruses following Sequential Immunization with Different Hemagglutinins", PLoS Pathogens, vol. 6, Issue 2, 9 pages, Feb. 2010.
Spiro et al. (Gen Bank: ABY81448.1, 2008).
Iowa State University Research Foundation, Inc., PCT/US17/59647 filed Nov. 2, 2017, "The International Search Report and the Written Opinion of the International Searching Authority, or the Declaration", 11 pages, mailed Jan. 18, 2018.

* cited by examiner

*Primary Examiner* — Agnieszka Boesen
(74) *Attorney, Agent, or Firm* — McKee, Voorhees & Sease, PLC

(57) ABSTRACT

The present invention provides vaccine or immunogenic compositions comprising novel antigens derived from the equine strain of influenza H3N8. These proteins and specific immunogenic domains are effective as primary universal influenza antigens. The disclosed vaccines or immunogenic compositions are highly effective in inducing HA specific antibodies reactive to different influenza viruses, mucosal and systemic immune responses, and cross-protection regardless of influenza virus subtypes. In some embodiments, the vaccine is cross-protective against two or more (e.g., 2, 3, 4, 5, or 6) subtypes of influenza with or without the use of an adjuvant.

19 Claims, 21 Drawing Sheets

Specification includes a Sequence Listing.

Nucleic Acids used in synthesis of H3N8 Kentucky 91 segment 4. Based on accession number CY028804 (SEQ ID NO:1)

ACTAAGCTTGGCCGCCACCAATGAAGACAACCATTATTTTGATACTACTGACCCATTGGGTCTACAGTCA
AAACCCAACCAGTGGCAACAACACAGCCACATTATGTCTGGGACACCATGCAGTAGCAAATGGAACATTG
GTAAAAACAATAACTGATGACCAAATTGAGGTGACAAATGCTACTGAATTAGTTCAGAGCATTTCAATAG
GGAAAATATGCAACAACTCATATAGAGTTCTAGATGGAAGAAATTGCACATTAATAGATGCAATGCTAGG
AGACCCCCACTGTGATGTCTTTCAGTATGAGAATTGGGACCTCTTCATAGAAAGAAGCAGCGCTTTCAGC
AGTTGCTACCCATATGACATCCCTGACTATGCATCGCTCCGGTCCATTGTAGCATCCTCAGGAACATTGG
AATTCACAGCAGAGGGATTCATATGGACAGGTGTCACTCAAAACGGAAGAAGTGGATCCTGCAAAAGGGG
ATCAGCCGATAGTTTCTTTAGCCGACTGAATTGGCTAACAAAATCTGGAAACTCTTACCCCACATTGAAT
GTGACAATGCCTAACAATAAAAATTTCGACAAACTATACATCTGGGGGATTCATCACCCGAGCTCAAACG
AAGAGCAGACAAAATTGTACATCCAAGAATCAGGACGAGTAACAGTCTCAACAAAAAGAAGTCAACAAAC
AATAATCCCTAACATCGGATCTAGACCGTGGGTCAGGGGTCAATCAGGCAGGATAAGCATATACTGGACC
ATTGTAAAACCTGGAGATATCCTAATGATAAACAGTAATGGCAACTTAGTTGCACCGCGGGGATATTTA
AATTGAAAACAGGGAAAAGCTCTGTAATGAGATCAGATGCACCCATAGACATTTGTGTGTCTGAATGTAT
TACACCAAATGGAAGCATCCCCAACGACAAACCATTTCAAAATGTGAACAAAGTTACATATGGAAAATGC
CCCAAGTATATCAGGCAAAACACTTTAAAGCTGGCCACTGGGATGAGGAATGTACCAGAAAAGCAAATCA
GAGGAATCTTTGGAGCAATAGCGGGATTCATAGAAAACGGCTGGGAAGGAATGGTTGATGGGTGGTATGG
ATTCCGATATCAAAACTCGGAAGGAACAGGACAAGCTGCAGATCTAAAGAGCACTCAAGCAGCCATCGAC
CAGATCAATGGAAAATTAAACAGAGTGATTGAAAGGACCAATGAGAAATTCCATCAAATAGAGAAGGAAT
TCTCAGAAGTAGAAGGGAGAATCCAGGACTTGGAGAAGTATGTAGAAGACACCAAAATAGACCTATGGTC
CTACAATGCAGAATTGCTGGTGGCTCTAGAAAATCAACATACAATTGACTTAACAGATGCAGAAATGAAT
AAATTATTCGAGAAGACTAGACGCCAGTTAAGAGAAAACGCGGAAGACATGGGAGGTGGATGTTTCAAGA
TATACCACAAATGTGATAATGCATGCATTGGATCAATAAGAAATGGGACATATGACCATTACATATACAG
AGATGAAGCATTAAACAACCGGTTTCAAATCAAAGGTGTTGAGTTGAAATCAGGCTACAAAGATTGGATA
CTGTGGATTTCATTCGCCATATCATGCTTCTTAATTTGCGTTGTTCTATTGGGTTTCATTATGTGGGCTT
GCCAAAAAGGCAACATCAGATGCAACATTTGCATTGAAAACCTGTACTTCCAGTCTGGTTCTGGTTACAT
CCCGGAAGCTCCGCGTGACGGTCAGGCGTACGTTCGTAAAGACGGTGAATGGGTTCTGCTGTCTACCTTC
CTGGGTCACCACCATCATCACCACTAACTCGAGAGGTACCTC

TRANSLATION (SEQ ID NO:2)

MKTIIILILLTHWVYSQNPTSGNNTATLCLGHHAVANGTLVKTI

TDGQIEVTNATELVQSTSIGKICNNPYRVLDGRNCTLIDAMLGDPHCDVFQYENWDLF

IERS*S*AFSNCYPYDIPDYASLRSIVASSGTLEFTAEGFIWTGVTQNGRSGACRRGSAD

SFFSRLNWLTKSGNSYPTLNVTMPNNNNFDKLYIWGIHHPSTNNEQTKLYIQESGRVT

VSTKRSQQTIIPNIGSRPWVRGQSGRISIYWTIVKPGDILMINSNGNLVAPRGYFKMR

TGKSSVMRS*D*APIDTCVSECITPNGSIPNDKPFQNVNKVTYGKCPKYIKQNTLKLATG

MRNVPEKQIRGIFGAIAGFIENGWEGMVDGWYGFRYQNSEGTGQAADLKSTQAAIDQI

NGKLNRVIERTNEKFHQIEKEFSEVEGRIQDLEKYVEDTKIDLWSYNAELLVALENQH

TIDLTDAEMNKLFEKTRRQLRENAEDMGGGCFKIYHKCDNACIGSIRNGTYDHYIYRD

EALNNRFQIKGVELKSGYKDWILWISFAISCFLICVVLLGFIMWACQKGNIRCNICI

SEQUENCE LISTING

Sequence total quantity: 2
SEQ ID NO: 1          moltype = DNA  length = 1725
FEATURE               Location/Qualifiers
source                1..1725
                      mol_type = genomic DNA

```
                        organism = Influenza A virus
CDS                     11..1708
                        protein_id = 2
                        translation = MKTIIILILLTHWVYSQNPTSGNNTATLCLGHHAVANGTLVKTITD
                         GQIEVTNATELVQSTSIGKICNNPYRVLDGRNCTLIDAMLGDPHCDVFQYENWDLFIER
                         SSAFSNCYPYDIPDYASLRSIVASSGTLEFTAEGFIWTGVTQNGRSGACRRGSADSFFS
                         RLNWLTKSGNSYPTLNVTMPNNNNFDKLYIWGIHHPSTNNEQTKLYIQESGRVTVSTKR
                         SQQTIIPNIGSRPWVRGQSGRISIYWTIVKPGDILMINSNGNLVAPRGYFKMRTGKSSV
                         MRSDAPIDTCVSECITPNGSIPNDKPFQNVNKVTYGKCPKYIKQNTLKLATGMRNVPEK
                         QIRGIFGAIAGFIENGWEGMVDGWYGFRYQNSEGTGQAADLKSTQAAIDQINGKLNRVI
                         ERTNEKFHQIEKEFSEVEGRIQDLEKYVEDTKIDLWSYNAELLVALENQHTIDLTDAEM
                         NKLFEKTRRQLRENAEDMGGGCFKIYHKCDNACIGSIRNGTYDHYIYRDEALNNRFQIK
                         GVELKSGYKDWILWISFAISCFLICVVLLGFIMWACQKGNIRCNICI
SEQUENCE: 1
tctgtcaatc atgaagacaa tcattatttt gatactactg acccattggg tctacagtca    60
aaacccaacc agtggcaaca acacagccac actatgtctg ggacaccatg cagtagcaaa   120
tggaacattg gtaaaaacaa taactgatgg ccaaattgag gtgacaaatg ctactgaatt   180
agttcagagc acttcaatag ggaaaatatg caacaaccca tatagggttc tagatggaag   240
aaactgcaca ttaatagatg caatgctagg agatccccac tgtgatgttt ttcagtatga   300
gaattgggac ctcttcatag aaagaagcag cgctttcagc aattgctacc catatgacat   360
ccctgactat gcatcgctcc ggtctattgt ggcatcttca ggaacattag aattcacagc   420
agagggattc atatggacag gtgtcactca aaacggaaga agtggagcct gcagaaggag   480
atcagccgat agtttcttta gccgactgaa ttggctaaca aaatctggaa attcttaccc   540
cacgttgaat gtgacaatgc ctaacaataa caatttcgat aaactataca tctgggggat   600
ccatcacccg agcacaaaca atgagcagac aaaattgtat atccaagaat cagggcgagt   660
aacagtctca caaaaaagaa gtcaacaaac aataatcccc aacatcggat ctagaccgtg   720
ggtcagggggt caatcaggca ggataagcat atattggacc attgtgaaac ctggagatat   780
cctaatgata aacagtaatg gcaacttagt tgcaccgcgg ggatatttca aaatgcggac   840
agggaaaagc tctgtaatga gatcagatgc acccatagac acttgtgtgt ccgagtgtat   900
tacaccaaat ggaagcatcc ccaacgacaa accattcaa aatgtgaaca aagttacata   960
tggaaaaatgc cccaagtata tcaagcagaa tactttgaag ctggccactg ggatgaggaa  1020
tgtaccagaa aagcaaatca gaggaatctt tggagcaata gcgggattca tagaaaacgg  1080
ctgggaagga atggttgatg ggtggtatgg attccgatat cagaattcgg aaggaacagg  1140
acaagctgca gatctaaaga gcactcaagc agccatcgac cagatcaatg gaaaattgaa  1200
cagagtgatt gagaggacca atgagaaatt ccatcaaata gagaaggaat tctcagaagt  1260
ggaagggaga atccaggact tggagaagta tgtagaagac accaaaatag acctatggtc  1320
ctacaatgca gaattactgg tggctctaga aaatcaacat acgattgact taacagatgc  1380
agagatgaat aaattattcg aaaagactag gcgccagtta agagaaaacg cggaagacat  1440
gggggggtgga tgtttcaaga tttatcacaa atgtgataat gcatgcattg gatcaataag  1500
aaatgggaca tatgaccatt acatatacag agatgaagca ttaaacaacc gatttcaaat  1560
taaaggtgtt gagttgaaat caggctacaa agattggata ctgtggattt cattcgccat  1620
atcatgcttc ttaatttgcg ttgttctatt gggtttcatc atgtgggctt gccaaaaagg  1680
caatatcaga tgcaacattt gcatttgagt aaactgatag ttaaa                  1725

SEQ ID NO: 2              moltype = AA   length = 565
FEATURE                   Location/Qualifiers
source                    1..565
                          mol_type = protein
                          organism = Influenza A virus
SEQUENCE: 2
MKTIIILILL THWVYSQNPT SGNNTATLCL GHHAVANGTL VKTITDGQIE VTNATELVQS    60
TSIGKICNNP YRVLDGRNCT LIDAMLGDPH CDVFQYENWD LFIERSSAFS NCYPYDIPDY   120
ASLRSIVASS GTLEFTAEGF IWTGVTQNGR SGACRRGSAD SFFSRLNWLT KSGNSYPTLN   180
VTMPNNNNFD KLYIWGIHHP STNNEQTKLY IQESGRVTVS TKRSQQTIIP NIGSRPWVRG   240
QSGRISIYWT IVKPGDILMI NSNGNLVAPR GYFKMRTGKS SVMRSDAPID TCVSECITPN   300
GSIPNDKPFQ NVNKVTYGKC PKYIKQNTLK LATGMRNVPE KQIRGIFGAI AGFIENGWEG   360
MVDGWYGFRY QNSEGTGQAA DLKSTQAAID QINGKLNRVI ERTNEKFHQI EKEFSEVEGR   420
IQDLEKYVED TKIDLWSYNA ELLVALENQH TIDLTDAEMN KLFEKTRRQL RENAEDMGGG   480
CFKIYHKCDN ACIGSIRNGT YDHYIYRDEA LNNRFQIKGV ELKSGYKDWI LWISFAISCF   540
LICVVLLGFI MWACQKGNIR CNICI                                        565
```

UNIVERSAL MAMMALIAN INFLUENZA VACCINE

CROSS-REFERENCE TO RELATED APPLICATIONS

This application is a Continuation of U.S. Ser. No. 16/400,817, filed May 1, 2019, which is a Continuation Application of PCT/US17/59647, filed Nov. 2, 2017, which claims priority under 35 U.S.C. § 119 to provisional application Ser. No. 62/416,466, filed Nov. 2, 2016, all of which are herein incorporated by reference in their entireties.

GRANT REFERENCE

This invention was made with Government support USDA/NIFA grant no. is NA/NI17AHDRXXXXG044. The Government has certain rights in the invention.

REFERENCE TO SEQUENCE LISTING SUBMITTED ELECTRONICALLY

The instant application contains a Sequence Listing which has been submitted electronically in XML format and is herein incorporated by reference in its entirety. Said XML copy, created on Jul. 31, 2023, is named "P12074US02_SequenceListing.xml" and is 6,250 bytes in size.

FIELD OF THE INVENTION

The present invention is generally directed to the field of influenza vaccines.

BACKGROUND OF THE INVENTION

Pandemic and seasonal influenza viruses continue as one of the largest public health concerns of the 21$^{st}$ century with seasonal strains responsible for 3-5 million severe infections and 500,000 deaths annually according to the World Health Organization. Vaccination remains the best defense, however, current vaccines have limited efficacy and provide extremely narrow breadth of protection. Moreover, influenza viruses evade immunity by continual antigenic variation of hemagglutinin (HA). Sporadic and highly lethal H5N1 infections in humans demonstrate a constant threat from viruses crossing the species barrier to endanger human health. Potentially pandemic strains such as H5N1, H7N2, H10N8, and H9H2 are circulating in permissive species with the possibility of mutations or reassortment with seasonal strains to allow infection of humans. The numbers of influenza strains (H1N1 and H3N2) that have crossed from birds into swine have dramatically increased in the last few years, further increasing the likelihood of crossing into humans. Thus, discovery of a universal vaccine that can elicit protective immune response against numerous strains is paramount for human health.

In addition to the threat posed to humans, influenza virus is one of the most significant disease pathogens of swine and a substantial economic threat to the pork industry. Like humans, swine are mainly infected by H1N1 and H3N2 viruses but remain under threat of potential cross-species infection from other strains such as H921 or H722 viruses. For H1 and H3 viruses, influenza strains are undergoing reassortment/drift while circulating through swine herds and these new reassortment viruses frequently cause outbreaks. Furthermore, like humans, H1N1 pnd09 still circulates and continues to infect swine. Cost estimates of influenza infection in swine show ~1.87% loss or $3.23 per head from morbidity or mortality over swine production without infection (without compounding effects of co-infections).

Influenza is a lipid-enveloped virus with a segmented negative sense RNA genome, which makes up three of the five genera of the family Orthomyxoviridae (Influenzavirus A, Influenzavirus B, and Influenzavirus C). Of the three types of influenza viruses, Influenza A viruses and Influenza B viruses are responsible for approximately 80% and 20% of influenza disease in humans, respectively. The Influenza A viruses are the most virulent human pathogens among the three influenza types and can be subdivided into different serotypes based on the antibody response to these viruses. Two types of surface glycoproteins, hemagglutinin (HA) and neuraminidase (NA), play essential roles in the viral infectivity. HA is responsible for attachment of the virus to sialic acid-containing receptors and viral entry by membrane fusion, whereas NA is a receptor-destroying enzyme which plays important roles in release of progeny virions from infected cells. There are 16 identified HA subtypes and 9 recognized NA subtypes, but only H1, H2, H3, and N1 and N2 are commonly found in humans. Genetic changes that occur in the surface glycoproteins every year, referred to as "antigenic drift", allow influenza viruses to evade the host immune system. Moreover, influenza viruses, in particular influenza A, can exchange genetic material and merge, a process known as "antigenic shift", which results in new strains different from both parent viruses, and can result in lethal pandemic strains.

Current influenza virus vaccines contain H1N1 (phylogenetic group 1 hemagglutinin), H3N2 (phylogenetic group 2 hemagglutinin), and 1-2 influenza B virus components. These vaccines are efficacious for closely matched strains by predominantly eliciting antibodies recognizing type specific epitopes in the globular head domain of Hemagglutinin. Currently licensed vaccines are comprised of cold adapted "attenuated" (LAIV), inactivated (TIV), and virosome delivery of influenza peptides. Only inactivated virus is licensed for swine. Also, TIV remains the most commonly administered vaccine but efficacy in children is generally quite poor, although even LAIV may fail to protect from infection as demonstrated by the failure of the 2013-14 H1N1 pnd09 component of the vaccine to protect from infection (CDC), or due to poor protection in general. The typical efficacy of influenza vaccines ranges from 40-69% (CDC) and may protect from disease but not infection. Thus, vaccinated children could spread the virus to their unvaccinated peers. As typified by the emergence of H1N1 pnd09 in the 2008-09 influenza season, strains can emerge late in the influenza season that vaccines based on earlier prediction strategies would fail to prevent.

Furthermore, mutations in the predicted strains can further limit the protection afforded by current influenza vaccines as typified by the H3N2v2 that emerged in 2012-13. Moreover, due to the limited efficacy of current influenza vaccine technology, predicting the next years relevant influenza strain or variance in antigenicity is not precise and vaccine miss-matches, antigenic variants and viral evolution of novel highly pathogenic strains such as avian H5N1, H7 and swine H1 and H3 variants complicate vaccine design. Mismatch vaccine failures and the pandemic threat from emergent viruses from reservoir hosts such as avian or swine viruses warrant the development of influenza A vaccines that provide broader depth of protection, such as a universal influenza vaccine capable of providing protection group 1

(H1, H2, H5, H6, H8, H9, H11, H12, H13, H16, H17) and group 2 influenza viruses (H3, H4, H7, H10, H14, H15).

Another important shortcoming of current vaccines is that high pathogen strains typically grow very slowly or not at all in the egg based vaccine system. Thus, if high pathologic strains cross the species divide, current technology for generating influenza vaccines (by reassortment or using similar strains) may not be fast enough to generate the necessary vaccine stocks to prevent/limit a potential pandemic. Thus there is an unmet need for immunogens that could foster cross-strain protection in humans and for immunogens that result in prevention of influenza in swine significantly reducing the risk of zoonotic infections.

BRIEF SUMMARY OF THE INVENTION

The present invention provides universal influenza vaccines capable of providing broad cross-strain protection. In particular, vaccine constructs designed to comprise novel antigens derived from the equine strain of influenza as primary universal influenza antigen are disclosed as are methods of using the same. In certain embodiments isolated form strain H3N8. In some embodiment the antigen includes at least one amino acid change so that the antigen is not the naturally occurring sequence. In certain embodiments the antigen is an immunogenic fragment thereof which includes the Arg 79, Asn 80; Ser 109 and Asp288 amino acids.

The disclosed H3 immunogen may be displayed on the surface of a particle. For example, the H3 immunogen may be expressed in a membrane-anchored form and incorporated in virus-like particles (VLPs). Alternatively, the H3 antigen is presented in a replicating live attenuated influenza virus vaccine. Therefore, a nucleic acid encoding the disclosed H3 antigen can be inserted in the genome of a replicating live attenuated influenza virus. Thus, also disclosed is a recombinant virus comprising a nucleic acid encoding a H3 antigen as disclosed herein.

The disclosed vaccines are highly effective in inducing HA specific antibodies reactive to different influenza viruses, mucosal and systemic immune responses, and cross-protection regardless of influenza virus subtypes. In some embodiments, the vaccine is cross-protective against two or more (e.g., 2, 3, 4, 5, or 6) subtypes of influenza with or without the use of an adjuvant. In addition, supplementing commercial human vaccines with the disclosed vaccine can significantly improve cross-protection.

In one embodiment, the disclosed vaccines are capable of preventing morbidity due to influenza infection in porcine. In another embodiment, the disclosed vaccines are capable of preventing influenza infection in porcine.

Also disclosed are isolated polynucleotides encoding the disclosed H3 antigens and cells containing these polynucleotides. In certain embodiments the polynucleotide includes one or more base changes so that the sequence is not a naturally occurring sequence. Also disclosed are methods of vaccinating a subject for influenza by administering to a subject in need thereof a composition comprising the disclosed vaccine. The disclosed vaccine may be administered alone or in combination with one or more additional influenza vaccines.

In one embodiment the invention provides kits comprising the immunogens, nucleic acid molecule, vectors, or vaccines of the present invention.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3A shows HAI titers were assessed across multiple strains of influenza. Line represents protective titer of 40. FIG. 3B shows microneutralization tested on the same sera using MDCK cells. There is no protective titer that is valid for this assay.

FIG. 5A shows cross-reactivity of murine sera to recombinant HAs were tested and found IgM responses bound multiple influenza groups. FIG. 5B shows HAI titers of mice vaccinated with equine H3N8. FIG. 5C shows HAI titers of mice vaccinated with trimeric Flumist (2012-2013). Point of note: the titer scales are not the same demonstrating clearly superior cross strain and titer activity in sera of mice vaccinated with H3N8. Bar shows a HAI of 40.

FIG. 8A shows H3N8 vaccinated mice were challenged with lethal dosage of H1N1 pnd09 (2000 TCID50). FIG. 8B shows H3N8 vaccinated mice were challenged with superlethal dosage of H3N2 X31 (100,000 TCID50). FIG. 8C shows sublethal dosages of H1N1 or H3N3 were used on vaccinated mice (H3N8 or H3N2).

FIG. 13 show nucleic acids used in synthesis of H3N8 Kentucky 91 segment 4. Based on accession number CY028804. (SEQ ID NO:1)

FIG. 14 shows PCR of infected Sf9 cells with baculovirus carrying either HA3 from equine H3N8 virus or RSV F or uninfected cells. These data show we have the recombinant HA to generate full length protein in insect cells.

FIG. 16A shows mice were vaccinated and then infected with either LAIV/Alum or PBS/BSA/Alum and infected with H1N1 New Caledonia using a sublethal infection. LAIV vaccinated mice showed no evidence of morbidity or infection (viral titers not shown). FIG. 16B shows additional vaccinated mice were challenged with a lethal dose (2LD50) using H3N2 Minnesota/10 v2. FIG. 16C shows additional vaccinated mice were challenged with a lethal dose (2LD50) using Solomon Is./3/06. (n=10 mice each). Survival had p<0.001

As shown in FIG. 4, our rHA vaccinees had higher titers to 1918 pandemic influenza.

DETAILED DESCRIPTION OF THE INVENTION

The following definitions and introductory matters are provided to facilitate an understanding of the present invention.

Figure 1:
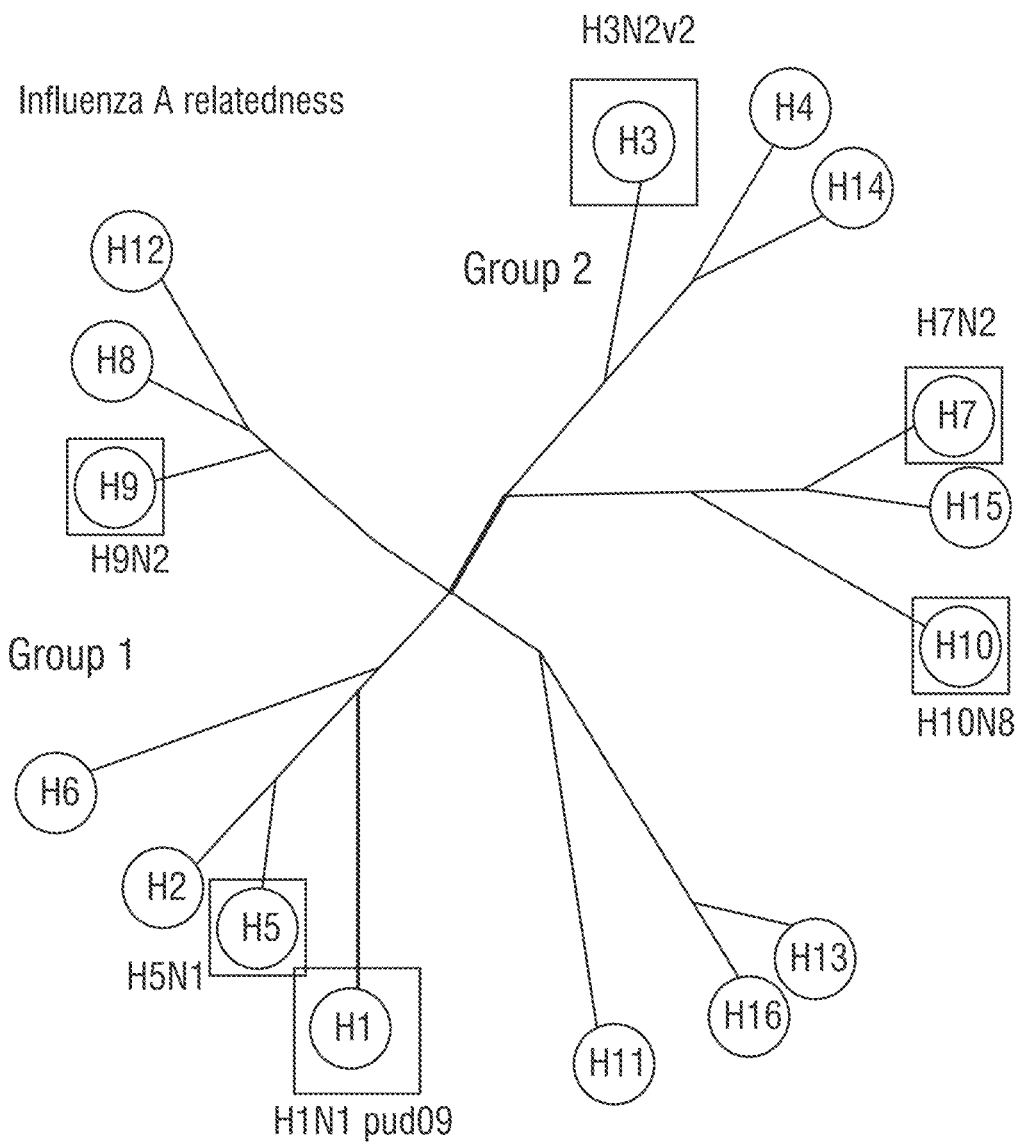
FIG. 1 shows the relatedness of influenza A subtypes. Hierarchy map of influenza subtypes was adapted from Nabel and Fauci, showing the various subtypes of influenza A. Red boxes identify typical human circulating subtypes. Yellow boxes indicate subtypes of pandemic concern. Strains below the boxes indicate strains within the boxes that are of immediate concern.

Due to limitations of current vaccines in inducing cross protection against antigenically distinct influenza viruses, a universal influenza vaccine that is based on the equine influenza H3 antigen is disclosed. Influenza is very diverse (FIG. 1) and capable of antigenic shift, making vaccination difficult. The typical approach to universal influenza vaccine design has been for testing various conformational formulations of HA to better generate Abs to the stalk region. Although recent progress has been made on this front, getting B-cells to target the HA stalk rather than the HA head has proven difficult. Current preclinical stem immunogens are expensive to manufacture of complicated to deliver. Since influenza vaccine compliance is already poor in people under the age of 65 years of age (~40-51% compliance, CDC), a universal vaccine that protects in the fewest number of vaccinations is ideal. Disclosed herein is are compositions and methods of making and using the same providing HA3 immunogens to be used in vaccines and/or as a supplement to stalk immunogens, which expose protective epitope(s), in the more immunogenic HA head region and elicit protective immune responses.

The present invention provides, according to one aspect, a method of improving the protective effect of an influenza vaccine by administering to a subject in need thereof a vaccine comprising equine H3 antigen or immunogenic fragments thereof, alone, prior to or together with an additional influenza vaccine. As demonstrated herein vaccination with equine H3 immunogens are particularly effective in eliciting anti-influenza immune responses (e.g., by increasing seroprotection as measured by Hemagglutination Inhibition (HAI)). Improved, HAI responses were directed not only against influenza strains whose HA were included but also against strains whose HA were not included in such vaccines, in addition to HAI response in distinct host species. These results are particularly surprising as to our knowledge a universal vaccine, as disclosed herein, capable of inducing protective immune response across multiple hemagglutinin subtypes (H1, H2, H3, H5, H7, etc.) or across Influenza types (type A, B, C) in any host species including human, swine or avian has not been reported.

Definitions

Unless otherwise noted, technical terms are used according to conventional usage. Definitions of common terms in molecular biology may be found in Benjamin Lewin, *Genes* X, published by Jones & Bartlett Publishers, 2009; and Meyers et al. (eds.), *The Encyclopedia of Cell Biology and Molecular Medicine*, published by Wiley-VCH in 16 volumes, 2008; and other similar references. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes.

Numeric ranges recited within the specification, including ranges of "greater than," "at least," or "less than" a numeric value, are inclusive of the numbers defining the range and include each integer within the defined range.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

"Optional" or "optionally" means that the subsequently described event or circumstance can or cannot occur, and that the description includes instances where the event of circumstance occurs and instances where is does not. For example, the phrase "optionally a signal peptide" means that the signal peptide may or may not be included.

The term "universal influenza vaccine" refers to a vaccine capable of providing cross-protection against at least two, including three, four, five or more, subtypes of influenza and/or across Influenza types, and/or in one or more host species.

A conventional seasonal vaccine typically contains three inactivated or live attenuated influenza virus strains and is therefore denoted also TIV (trivalent influenza vaccine). The three strains are selected each year by the WHO to provide protection against the strains that are expected to infect in the coming season A pandemic vaccine typically includes one influenza virus strain specific to the relevant strain causing the pandemic. For example, The A/H1N1 strain used for swine flu pandemic during 2009/2010 season, was then included in the seasonal TIV formulation in the 2010/2011 season.

Seroconversion and seroprotection: seroconversion to HA antibodies is measured in an HAI assay which is the test accepted by the regulatory authorities to correlate with protection against influenza infection. Serial two-fold dilutions of serum collected from vaccinated subjects are incubated with the test viruses to determine the dilution at which inhibition of unbound erythrocyte agglutination no longer occurs. The reciprocal of the dilution at which this occurs is then defined as the HAI titer. Subjects are considered seroconverted toward a specific influenza virus when the fold increase in HAI titers is ≥4-fold from that of baseline titers as measured in sera collected on day 0 of the study.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

As used herein, "adjuvant" means a vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Non-limiting Exemplary adjuvants include Th17 adjuvants (e.g. IL-17), or IL-IL-2, RANTES, GM-CSF, and TNF-a, IFN-γ, G-CSF, LFA-3, CD72, B7-1, B7-2, OX-40 L, 4-1BBL and toll-like receptor (TLR) agonists, such as TLR-9 agonists. In some embodiments, the ADJUPLEX™ (Advanced BioAdjuvants) can be used with any of the immunogens of the present invention to elicit an immune response producing bnAbs. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed immunogens.

As used herein, the term "administration" refers to the introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

As used herein, "nucleic acid" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

The term "variant" refers to an amino acid sequence having conservative amino acid substitutions, non-conservative amino acid substitutions (i.e. a degenerate variant), or a peptide having 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the recited sequence. The term "conservatively modified variants" applies to both amino acid and nucleic acid sequences. With respect to particular nucleic acid sequences, a conservatively modified variant refers to those nucleic acids, which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid, which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, generation of immune response, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids, which are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company. Further, the term "amino acid substitutions" means the replacement of one amino acid in a polypeptide with a different amino acid or with no amino acid (i.e., a deletion).

The term "percent (%>)sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, "contacting" refers to the placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

The term "immunogenicity" or "immunogenic" relates to the ability of a substance to stimulate or elicit an immune response. Immunogenicity is measured, for example, by determining the presence of antibodies specific for the substance. The presence of antibodies is detected by methods known in the art, for example using an ELISA or HAI assay.

As used herein an "immunogenic composition" refers to a composition comprising an immunogenic polypeptide, or a nucleic acid molecule or vector encoding an immunogenic polypeptide that induces a measurable CTL response against the immunogenic polypeptide, or induces a measurable B cell response (such as production of antibodies) against the immunogenic polypeptide. In one example, an "immunogenic composition" is a composition that includes a disclosed recombinant or synthesized equine H3 or immunogenic fragment thereof, that induces a measurable CTL response against an influenza virus, or induces a measurable B cell response (such as production of antibodies) against influenza. It further refers to isolated nucleic acids encoding an antigen, such as a nucleic acid that can be used to express the antigen (and thus be used to elicit an immune response against this peptide). For in vitro use, an immunogenic composition may comprise or consist of the isolated protein or nucleic acid molecule encoding the protein. For in vivo use, the immunogenic composition will typically include the protein or nucleic acid molecule in a pharmaceutically acceptable carrier and may also include other agents, such as an adjuvant. Any particular protein, such as a disclosed recombinant or synthesized equine H3 or immunogenic fragment thereof, or a nucleic acid encoding the protein, can be readily tested for its ability to induce a CTL or B cell response by art-recognized assays. Immunogenic compositions can include adjuvants, which are well known to one of skill in the art.

As used herein, "immunogenic polypeptide" refers to a polypeptide which comprises an allele-specific motif, an epitope or other sequence such that the polypeptide will bind an MHC molecule and induce an immune response, such as a cytotoxic T lymphocyte ("CTL") response, and/or a B cell response (for example, antibody production), and/or a T-helper lymphocyte response against the antigen from which the immunogenic polypeptide is derived. The term "antigen presentation" means the expression of antigen on the surface of a cell in association with major histocompatibility complex class I or class II molecules (MHC-I or MHC-II) of animals or with the HLA-I and HLA-II of humans.

An "isolated" biological component (such as a protein, for example a disclosed immunogen or nucleic acid encoding such an antigen) has been substantially separated or purified away from other biological components, such as other biological components in which the component naturally occurs, such as other chromosomal and extrachromosomal DNA, RNA, and proteins. Proteins, peptides and nucleic acids that have been "isolated" include proteins purified by standard purification methods. The term also embraces proteins or peptides prepared by recombinant expression in a host cell as well as chemically synthesized proteins, peptides and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

As used herein, "antibody" means an immunoglobulin, antigen-binding fragment, or derivative thereof, which specifically binds and recognizes an analyte (antigen) such as influenza HA peptide, an antigenic fragment thereof, or a dimer or multimer of the antigen. The term "antibody" is used herein in the broadest sense and encompasses various antibody structures, including but not limited to monoclonal antibodies, polyclonal antibodies, multi-specific antibodies (e.g., bi-specific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), *Antibody Engineering*, Vols. 1-2, 2nd Ed., Springer Press, 2010).

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (□) and kappa (□). There are five main heavy chain classes (or isotypes) which determine the functional activity of an antibody molecule: IgM, IgD, IgG, IgA and IgE.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space. The CDRs are primarily responsible for binding to an epitope of an antigen.

A "monoclonal antibody" is an antibody produced by a single clone of B-lymphocytes or by a cell into which nucleic acid encoding the light and heavy chains of a single antibody have been transfected, or a progeny thereof. Monoclonal antibodies are produced by methods known to those of skill in the art, for instance by making hybrid antibody-forming cells from a fusion of myeloma cells with immune spleen cells. These fused cells and their progeny are termed "hybridomas." In some examples monoclonal antibodies are isolated from a subject. Monoclonal antibodies can have conservative amino acid substitutions which have substantially no effect on antigen binding or other immunoglobulin functions. (See, for example, Harlow & Lane, Antibodies, A Laboratory Manual, 2nd ed. Cold Spring Harbor Publications, New York (2013).)

As used herein, the term "antigen" refers to a compound, composition or substance that can stimulate the production of antibodies or a T cell response in an animal, including compositions that are injected or absorbed into an animal. An antigen reacts with the products of specific humoral or cellular immunity, including those induced by heterologous or synthesized antigens, such as the disclosed equine H3 antigen. Examples of antigens include, but are not limited to, polypeptides, peptides, lipids, polysaccharides, combinations thereof (such as glycopeptides) and nucleic acids containing antigenic determinants, such as those recognized by an immune cell. In some examples, antigens include peptides derived from a pathogen of interest, such as influenza virus. An antigen can include one or more epitopes.

A "neutralizing antibody" refers to an antibody which reduces the infectious titer of an infectious agent by binding to a specific antigen on the infectious agent. In some examples the infectious agent is a virus. In some examples, an antibody that is specific for HA and neutralizes the infectious titer of influenza virus. A "broadly neutralizing antibody" is an antibody that binds to and inhibits the function of related antigens, such as antigens that share at least 65%, 75%, 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen. For example, with regard to the influenza virus, the antibody can bind to and inhibit the function of an antigen, such as HA from more than one serotype and/or Influenza type. In one embodiment, broadly neutralizing antibodies to influenza virus are distinct from other antibodies to influenza in that they neutralize a high percentage of the many types of influenza virus in circulation.

Influenza epitopes can be classified as B-cell type, T-cell type or both B cell and T cell type, depending on the type of immune response they elicit. The definition of B cell or T cell peptide epitope is not unequivocal; for example, a peptide epitope can induce antibody production but at the same time that epitope can possess a sequence that enables binding to the human HLA molecule, rendering it accessible to CTLs, hence a dual B cell and T cell classification for that particular epitope. "CTL", "killer T cells" or "cytotoxic T cells" is a group of differentiated T cells that recognize and lyse target cells bearing a specific foreign antigen that function in defense against viral infection and cancer cells. "T helper cell" or "Th" is any of the T cells that when stimulated by a specific antigen release cytokines that promote the activation and function of B cells and killer T cells.

An "epitope" is an antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on equine H3 antigen.

As used herein "expression" refers to transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA.

In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression control sequences refer to nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., Methods in Enzymology 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

As used herein, "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adena-associated viruses) that incorporate the recombinant polynucleotide.

The term "heterologous" as used herein describes a relationship between two or more elements which indicates that the elements are not normally found in proximity to one another in nature. Thus, for example, a polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g., a genetically engineered coding sequence or an allele from a different ecotype or variety). An example of a heterologous polypeptide is a polypeptide expressed from a recombinant polynucleotide in a transgenic organism. Heterologous polynucleotides and polypeptides are forms of recombinant molecules. In one specific, non-limiting example, a heterologous nucleic acid molecule encoding a recombinant H3 antigen or immunogenic fragment thereof, is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

By "host cell" is meant a cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

As used herein, "immune response" refers to a response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to pre-treatment of a subject with an adjuvant to increase the desired immune response to a later administered immunogenic agent. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

As used herein, "immunogen" refers to a protein or a portion thereof that is capable of inducing an immune response in a mammal, such as a mammal infected or at risk of infection with a pathogen. An appropriate immunogenic preparation can contain, for example, a recombinantly expressed or a chemically synthesized polypeptide (e.g. synthesized by cell-free protein synthesis). Administration of an immunogen can lead to protective immunity and/or proactive immunity against a pathogen of interest. In some examples, an immunogen comprises a recombinant or synthesized equine H3 antigen or immunogenic fragment thereof, as disclosed herein.

The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, "operably linked" is a first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

"Polypeptide modifications" refers to polypeptides and peptides, such as the recombinant or synthesized equine H3 proteins disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C16 alkyl or dialkyl amino or further converted to an amide. Hydroxyl groups of the peptide side chains can be converted to C1-C16 alkoxy or to a C1-C16 ester using well-recognized techniques. Phenyl and phenolic rings of the peptide side chains can be substituted with one or more halogen atoms, such as F, Cl, Br or I, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

"Prime-boost vaccination" is an immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; the skilled artisan will understand a suitable time interval between administration of the primer vaccine and the booster vaccine. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein subunit or protein nanoparticle based vaccine.

As used herein, "recombinant" refers to a nucleic acid that has a sequence that is not naturally occurring or has a sequence that is made by an artificial combination of two otherwise separated segments of sequence. This artificial combination can be accomplished, for example, the artificial manipulation of isolated segments of nucleic acids, for example using genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

The term "vector" refers to a nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

"Virus-like particle" (VLP) is a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) Biophys. J. 60:1445-1456; and Hagensee et al. (1994) J. Viral. 68:4503-4505; Vincente, J Invertebr Pathol., 2011; Schneider Ohrum and Ross, Curr. Top. Microbial. Immunol., 354: 53073, 2012).

A "sample (or biological sample) is a biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material.

HA3 Immunogen

In one aspect, the present invention involves a vaccine comprising heterologous equine HA3 epitope(s) sequences molecularly designed to elicit anti-influenza immune response covering a broad range of antigenically different subtypes of influenza viruses. For example, the HA3 epitope (s) sequences can be elicit protective immune responses to human, swine, avian influenza strains, or any combination thereof.

In one embodiment, provides equine HA3 immunogen of the present invention encoded by the nucleic acid SEQ ID NO: 1 or a conservative variant thereof having at least 70%, 73%, 76%, 79%, 82%, 85%, 88%, 91%, 94%, or 97% sequence identity to SEQ ID NO: 1. In a further aspect of the invention provides equine HA3 immunogen peptide comprising SEQ ID NO: 2 or a conservative variant thereof having at least 70%, 73%, 76%, 79%, 82%, 85%, 88%, 91%, 94%, or 97% sequence identity to SEQ ID NO: 2.

The HA3 immunogenic peptides and polypeptides of the present invention may be synthesized chemically using methods known in the art for synthesis of peptides, peptide multimers and polypeptides. These methods generally rely on the known principles of peptide synthesis; most conveniently, the procedures can be performed according to the known principles of solid phase peptide synthesis.

Peptide analogs and peptidomimetics are also included within the scope of the invention as well as salts and esters of the peptides of the invention are encompassed. A peptide analog according to the present invention may optionally comprise at least one non-natural amino acid and/or at least one blocking group at either the C terminus or N terminus. Salts of the peptides of the invention are physiologically acceptable organic and inorganic salts. The design of appropriate "analogs" may be computer assisted.

The term "peptidomimetic" means that a peptide according to the invention is modified in such a way that it includes at least one non-peptidic bond such as, for example, urea bond, carbamate bond, sulfonamide bond, hydrazine bond, or any other covalent bond. The design of appropriate "peptidomimetic" may be computer assisted.

Salts and esters of the peptides of the invention are encompassed within the scope of the invention. Salts of the peptides of the invention are physiologically acceptable organic and inorganic salts. Functional derivatives of the peptides of the invention covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide and do not confer toxic properties on compositions containing it. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

Also disclosed are polynucleotides comprising nucleic acid sequences encoding the disclosed HA3 immunogen. For example, the nucleic acid sequences can be operably linked to expression control sequences. Thus, also disclosed are expression vectors for producing the disclosed H3 antigens as well as cells containing these polynucleotides and vectors for replicating the polynucleotides and vectors or to produce the disclose equine H3 proteins and/or VLPs and/or inactivated/attenuated live or killed viruses. Therefore, the disclosed cell can also contain nucleic acid sequences encoding an HA3 protein, including a vector comprising the nucleic acid sequences encoding an HA3 protein.

The cell can be a prokaryotic or eukaryotic cell. For example, the cell can be a bacterium, an insect cell, a yeast cell, or a mammalian cell. The cell can be a human cell. Suitable vectors can be routinely selected based on the choice of cell used to produce the VLP. For example, where insect cells are used, suitable vectors include baculoviruses.

Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins.

In a non-limiting example, the chimeric polypeptide of the present invention includes chimeras of an influenza peptide epitope with one of the following, polypeptides: Cholera toxin, Tetanus toxin, Ovalbumin, Tuberculosis heat shock protein, Diphtheria Toxoid, Protein G from respiratory syncytial virus, Outer Membrane Protein from *Neisseria meningitides*, nucleoprotein of vesicular stomatitis virus, glycoprotein of vesicular stomatitis virus, *Plasmodium falciparum* Antigen Glutamate-Rich Protein, Merozoite Surface Protein 3 or Viruses envelope protein.

The term "expression vector" and "recombinant expression vector" as used herein refers to a DNA molecule, for example a plasmid or virus, containing a desired and appropriate nucleic acid sequences necessary for the expression of the recombinant peptide epitopes for expression in a particular host cell. As used herein "operably linked" refers to a functional linkage of at least two sequences. Operably linked includes linkage between a promoter and a second sequence, for example an nucleic acid of the present invention, wherein the promoter sequence initiates and mediates transcription of the DNA sequence corresponding to the second sequence.

The regulatory regions necessary for transcription of the peptide epitopes can be provided by the expression vector. The precise nature of the regulatory regions needed for gene expression may vary among vectors and host cells. Generally, a promoter is required which is capable of binding RNA polymerase and promoting the transcription of an operably-associated nucleic acid sequence. Regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites. A translation initiation codon (ATG) may also be provided.

In order to clone the nucleic acid sequences into the cloning site of a vector, linkers or adapters providing the appropriate compatible restriction sites are added during, synthesis of the nucleic acids. For example, a desired restriction enzyme site can be introduced into a fragment of DNA by amplification of the DNA by use of PCR with primers containing the desired restriction enzyme site.

An expression construct comprising a peptide epitope sequence operably associated with regulatory regions can be directly introduced into appropriate host cells for expression and production of the HA3 multiepitope polypeptide per se or as recombinant H3 immunogen. The expression vectors that may be used include but are not limited to plasmids, cosmids, phage, phagemids, flagellin or modified viruses. Typically, such expression vectors comprise a functional origin of replication for propagation of the vector in an appropriate host cell, one or more restriction endonuclease sites for insertion of the desired gene sequence, and one or more selection markers.

The recombinant polynucleotide construct comprising the expression vector and a HA3 polypeptide should then be transferred into a bacterial host cell where it can replicate and be expressed. This can be accomplished by methods known in the art. The expression vector is used with a compatible prokaryotic or eukaryotic host cell which may be derived from bacteria, yeast, insects, mammals and humans.

Production of the HA3 Immunogenic Polypeptide

Once expressed by the host cell, the HA3 polypeptide can be separated from undesired components by a number of protein purification methods. One such method uses a polyhistidine tag on the recombinant protein. A polyhistidine-tag consists in at least six histidine (His) residues added to a recombinant protein, often at the N- or C-terminus Polyhistidine-tags are often used for affinity purification of polyhistidine-tagged recombinant proteins that are expressed in *E. coli* or other prokaryotic expression systems. The bacterial cells are harvested by centrifugation and the resulting cell pellet can be lysed by physical means or with detergents or enzymes such as lysozyme. The raw lysate contains at this stage the recombinant protein among several other proteins derived from the bacteria and are incubated with affinity media such as NTA-agarose, HisPur resin or Talon resin. These affinity media contain bound metal ions, either nickel or cobalt to which the polyhistidine-tag binds with micromolar affinity. The resin is then washed with phosphate buffer to remove proteins that do not specifically interact with the cobalt or nickel ion. The washing efficiency can be improved by the addition of 20 mM imidazole and proteins are then usually eluted with 150-300 mM imidazole. The polyhistidine tag may be subsequently removed using restriction enzymes, endoproteases or exoproteases. Kits for the purification of histidine-tagged proteins can be purchased for example from Qiagen.

Another method is through the production of inclusion bodies, which are inactive aggregates of protein that may form when a recombinant polypeptide is expressed in a prokaryote. While the cDNA may properly code for a translatable mRNA, the protein that results may not fold correctly, or the hydrophobicity of the added peptide epitopes may cause the recombinant polypeptide to become insoluble. Inclusion bodies are easily purified by methods well known in the art. Various procedures for the purification of inclusion bodies are known in the art. In some embodiments the inclusion bodies are recovered from bacterial lysates by centrifugation and are washed with detergents and chelating agents to remove as much bacterial protein as possible from the aggregated recombinant protein. To obtain soluble protein, the washed inclusion bodies are dissolved in denaturing agents and the released protein is then refolded by gradual removal of the denaturing reagents by dilution or dialysis (as described for example in Molecular cloning: a laboratory manual, 3rd edition, Sambrook, J. and Russell, D. W., 2001; CSHL Press).

Virus Like Particles (VLPs)

The disclosed HA3 immunogenic sequences may be expressed on the surface of a particle to mimic the natural conformation of HA3 on influenza virions. For example, the disclosed H3 antigens may be incorporated into virus-like particles (VLPs). Non-replicating VLPs resemble infectious virus particles in structure and morphology, and contain immunologically relevant viral structural proteins. VLPs have been produced from both non-enveloped and enveloped viruses. Envelopes of VLPs are derived from the host cells similar to the way as enveloped viruses such as influenza A virus obtain their lipid envelopes from their host cells. Therefore, membrane-anchored proteins on the surfaces of enveloped viruses will be expressed in a native-like conformation if they are expressed in a membrane-anchored form.

Influenza VLPs involve lipid bilayers and host cell membrane proteins (Song, J. M., et al. J Proteome Res 2011 10:3450-3459). For example, Influenza VLPs containing the wild type M2 protein have been described (Song, J. M., et al. Proc Natl Acad Sci USA 2011 108:757-761; Song, J. M., et al. PLoS One 2011 6:e14538). Enveloped VLPs may be composed of influenza matrix 1 (M1) protein as a particle forming core. These VLPs are produced, for example, by coinfecting insect cells with one or more recombinant baculoviruses co-expressing M1 proteins and the disclosed H3 antigens, culturing the insect cells under physiological conditions, and purifying the VLPs from insect cell culture supernatants.

Vaccine Formulation

The vaccines of the present invention comprise a HA3 immunogenic polypeptide or a recombinant H3 protein comprising a multi-epitope polypeptide, and optionally, an adjuvant. The vaccine can be formulated for administration in one of many different modes. In one embodiment, the vaccine is formulated for parenteral administration. In some embodiments the vaccine is formulated for mass inoculation, for example for use with a jet-injector or a single use cartridge. According to one embodiment of the invention, the vaccine administration is intramuscular. According to another embodiment the administration is intradermal. Needles specifically designed to deposit the vaccine intradermally are known in the art as disclosed for example in U.S. Pat. Nos. 6,843,781 and 7,250,036 among others. According to other embodiments the administration is performed with a needleless injector.

According to yet another embodiment the vaccine is administered intranasally. The vaccine formulation may be applied to the lymphatic tissue of the nose in any convenient manner. However, it is preferred to apply it as a liquid stream or liquid droplets to the walls of the nasal passage. The intranasal composition can be formulated, for example, in liquid form as nose drops, spray, or suitable for inhalation, as powder, as cream, or as emulsion. The composition can contain a variety of additives, such as adjuvant, excipient, stabilizers, buffers, or preservatives.

For straightforward application, the vaccine composition is preferably supplied in a vessel appropriate for distribution of the polypeptide or recombinant H3 immunogen in the form of nose drops or an aerosol. In certain preferred embodiments the vaccine is formulated for mucosal delivery, in particular nasal delivery (Amon et al., Biologicals. 2001; 29(3-4):237-42; Ben-Yedidia et al., Int Immunol. 1999; 11(7):1043-51).

In another embodiment of the invention, administration is oral and the vaccine may be presented, for example, in the form of a tablet or encased in a gelatin capsule or a microcapsule. The formulation of these modalities is general knowledge to those with skill in the art.

Liposomes provide another delivery system for antigen delivery and presentation. Liposomes are bilayered vesicles composed of phospholipids and other sterols surrounding a typically aqueous center where antigens or other products can be encapsulated. The liposome structure is highly versatile with many types range in nanometer to micrometer sizes, from about 25 nm to about 50 µm. Liposomes have been found to be effective in delivering therapeutic agents to dermal and mucosal surfaces. Liposomes can be further modified for targeted delivery by for example, incorporating specific antibodies into the surface membrane, or altered to encapsulate bacteria, viruses or parasites. The average survival time or half life of the intact liposome structure can be extended with the inclusion of certain polymers, for example polyethylene glycol, allowing for prolonged release in vivo. Liposomes may be unilamellar or multilamellar.

The vaccine composition may be formulated by: encapsulating an antigen or an antigen/adjuvant complex in liposomes to form liposome-encapsulated antigen and mixing the liposome-encapsulated antigen with a carrier comprising a continuous phase of a hydrophobic substance. If an antigen/adjuvant complex is not used in the first step, a suitable adjuvant may be added to the liposome-encapsulated antigen, to the mixture of liposome-encapsulated antigen and carrier, or to the carrier before the carrier is mixed with the liposome-encapsulated antigen. The order of the process may depend on the type of adjuvant used. Typically, when an adjuvant like alum is used, the adjuvant and the antigen are mixed first to form an antigen/adjuvant complex followed by encapsulation of the antigen/adjuvant complex with liposomes. The resulting liposome-encapsulated antigen is then mixed with the carrier. The term "liposome-encapsulated antigen" may refer to encapsulation of the antigen alone or to the encapsulation of the antigen/adjuvant complex depending on the context. This promotes intimate contact between the adjuvant and the antigen and may, at least in part, account for the immune response when alum is used as the adjuvant. When another is used, the antigen may be first encapsulated in liposomes and the resulting liposome-encapsulated antigen is then mixed into the adjuvant in a hydrophobic substance.

In formulating a vaccine composition that is substantially free of water, antigen or antigen/adjuvant complex is encapsulated with liposomes and mixed with a hydrophobic substance. In formulating a vaccine in an emulsion of water-in-a hydrophobic substance, the antigen or antigen/adjuvant complex is encapsulated with liposomes in an aqueous medium followed by the mixing of the aqueous medium with a hydrophobic substance. In the case of the emulsion, to maintain the hydrophobic substance in the continuous phase, the aqueous medium containing the liposomes may be added in aliquots with mixing to the hydrophobic substance.

In all methods of formulation, the liposome-encapsulated antigen may be freeze-dried before being mixed with the hydrophobic substance or with the aqueous medium as the case may be. In some instances, an antigen/adjuvant complex may be encapsulated by liposomes followed by freeze-drying. In other instances, the antigen may be encapsulated by liposomes followed by the addition of adjuvant then freeze-drying to form a freeze-dried liposome-encapsulated antigen with external adjuvant. In yet another instance, the antigen may be encapsulated by liposomes followed by freeze-drying before the addition of adjuvant. Freeze-drying may promote better interaction between the adjuvant and the antigen resulting in a more efficacious vaccine.

Formulation of the liposome-encapsulated antigen into a hydrophobic substance may also involve the use of an emulsifier to promote more even distribution of the liposomes in the hydrophobic substance. Typical emulsifiers are well-known in the art and include mannide oleate (Arlacel™ A), lecithin, Tween™ 80, Spans™ 20, 80, 83 and 85. The emulsifier is used in an amount effective to promote even distribution of the liposomes. Typically, the volume ratio (v/v) of hydrophobic substance to emulsifier is in the range of about 5:1 to about 15:1.

Microparticles and nanoparticles employ small biodegradable spheres which act as depots for vaccine delivery. The major advantage that polymer microspheres possess over other depot-effecting adjuvants is that they are extremely safe and have been approved by the Food and Drug Administration in the US for use in human medicine as suitable sutures and for use as a biodegradable drug, delivery system (Langer R. Science. 1990, 249, 1527). The rates of copolymer hydrolysis are very well characterized, which in turn allows for the manufacture of microparticles with sustained antigen release over prolonged periods of time (O'Hagen, et al., Vaccine. 1993, 11, 965).

Parenteral administration of microparticles elicits long-lasting immunity, especially if they incorporate prolonged release characteristics. The rate of release can be modulated by the mixture of polymers and their relative molecular weights, which will hydrolyze over varying periods of time. Without wishing to be bound to theory, the formulation of different sized particles (1 μm to 200 μm) may also contribute to long-lasting immunological responses since large particles must be broken down into smaller particles before being available for macrophage uptake. In this manner a single-injection vaccine could be developed by integrating various particle sizes, thereby prolonging antigen presentation and greatly benefiting livestock producers.

In some applications an adjuvant or excipient may be included in the vaccine formulation. Montanide™ and alum for example, are preferred adjuvants for human use. The choice of the adjuvant will be determined in part by the mode of administration of the vaccine. For example, non-injected vaccination will lead to better overall compliance and lower overall costs. A preferred mode of administration is intramuscular administration. Another preferred mode of administration is intranasal administration. Non-limiting examples of intranasal adjuvants include chitosan powder, PLA and PLG microspheres, QS-21, calcium phosphate nanoparticles (CAP) and mCTA/LTB (mutant cholera toxin. E112K with pentameric B subunit of heat labile enterotoxin).

According to several embodiments, the vaccine compositions according to the present invention may contain one or more adjuvants, characterized in that it is present as a solution or emulsion which is substantially free from inorganic salt ions, wherein said solution or emulsion contains one or more water soluble or water-emulsifiable substances which is capable of making the vaccine isotonic or hypotonic. The water soluble or water-emulsifiable substances may be, for example, selected from the group consisting of: maltose; fructose; galactose; saccharose; sugar alcohol; lipid; and combinations thereof.

The formulations of the present invention may optionally comprise a mucosal delivery-enhancing agent such as for example a permeabilizing peptide that reversibly enhances mucosal epithelial paracellular transport by modulating epithelial junctional structure and/or physiology, as described in US 2004/0077540.

The HA3 immunogenic polypeptides used in the methods and compositions of the present invention comprise according to several specific embodiments a proteosome adjuvant. The proteosome adjuvant comprises a purified preparation of outer membrane proteins of meningococci and similar preparations from other bacteria. These proteins are highly hydrophobic, reflecting their role as transmembrane proteins and porins. Due to their hydrophobic protein-protein interactions, when appropriately isolated, the proteins form multi-molecular structures consisting of about 60-100 nm diameter whole or fragmented membrane vesicles. This liposome-like physical state allows the proteosome adjuvant to act as a protein carrier and also to act as an adjuvant. Polypeptides used according to the present invention are optionally complexed to the proteosome antigen vesicles through hydrophobic moieties. For example, an antigen is conjugated to a lipid moiety such as a fatty acyl group. Such a hydrophobic moiety may be linked directly to the HA3 immunogenic polypeptide or alternatively, a short spacer, for example, of one, two, three or four, up to six or ten amino acids can be used to link the HA3 polypeptide to the fatty group. This hydrophobic anchor interacts with the hydrophobic membrane of the proteosome adjuvant vesicles, while presenting the generally hydrophilic antigenic peptide.

In particular, a hydrophobic anchor may comprise a fatty acyl group attached to the amino terminus or near the carboxyl terminus of the HA3 immunogenic polypeptide. One example is the twelve-carbon chain lauroyl ($CH_3(CH)_{10}CO$), although any similarly serving fatty acyl group including, but not limited to, acyl groups that are of eight-, ten-, fourteen-, sixteen-, eighteen-, or twenty-carbon chain lengths can also serve as hydrophobic anchors. The anchor may be linked to the peptide antigen using an immunopotentiating spacer. Such a linker may consist of 1-10 amino acids, which may assist in maintaining the conformational structure of the peptide.

The antigen content is best defined by the biological effect it provokes. Naturally, sufficient antigen should be present to provoke the production of measurable amounts of protective antibody. A convenient test for the biological activity of viruses involves the ability of the antigenic material undergoing testing to deplete a known positive antiserum of its protective antibody. The result is reported in the negative log of the LD50 (lethal dose, 50%) for mice treated with virulent organisms which are pretreated with a known antiserum which itself was pretreated with various dilutions of the antigenic material being evaluated. A high value is therefore reflective of a high content of antigenic material which has tied up the antibodies in the known antiserum thus reducing or eliminating the effect of the antiserum on the virulent organism making a small dose lethal. It is preferred that the antigenic material present in the final formulation is at a level sufficient to increase the negative log of LD50 by at least 1 preferably 1.4 compared to the result from the virulent organism treated with untreated antiserum. The absolute values obtained for the antiserum control and suitable vaccine material are, of course, dependent on the virulent organism and antiserum standards selected.

The following method may be also used to achieve the ideal vaccine formulation: starting from a defined antigen, which is intended to provoke the desired immune response, in a first step an adjuvant matched to the antigen is found, as described in the specialist literature, particularly in WO 97/30721. In a next step the vaccine is optimized by adding various isotonic-making substances as defined in the present inventions, preferably sugars and/or sugar alcohols, in an isotonic or slightly hypotonic concentration, to the mixture of antigen and adjuvant, with the composition otherwise being identical, and adjusting the solution to a physiological pH in the range from pH 4.0 to 10.0, particularly 7.4. Then, in a first step the substances or the concentration thereof which will improve the solubility of the antigen/adjuvant composition compared with a conventional, saline-buffered solution are determined. The improvement in the solubility characteristics by a candidate substance is a first indication that this substance is capable of bringing about an increase in the immunogenic activity of the vaccine.

Since one of the possible prerequisites for an increase in the cellular immune response is increased binding of the antigen to APCs (antigen presenting cells), in a next step an investigation can be made to see whether the substance leads to an increase of this kind. The procedure used may be analogous to that described in the definition of the adjuvant, e.g. incubating APCs with fluorescence-labelled peptide or protein, adjuvant and isotonic-making substance. An increased uptake or binding of the peptide to APCs brought about by the substance can be determined by comparison with cells which have been mixed with peptide and adjuvant alone or with a peptide/adjuvant composition which is present in conventional saline buffer solution, using throughflow cytometry.

In a second step the candidate substances may be investigated in vitro to see whether and to what extent their presence is able to increase the presentation of a peptide to APCs; the MHC concentration on the cells may be measured using the methods described in WO 97/30721 for testing peptides.

Another possible way of testing the efficiency of a formulation is by using an in vitro model system. In this, APCs are incubated together with adjuvant, peptide and candidate substance and the relative activation of a T-cell clone which specifically recognizes the peptide used is measured (Coligan et al., 1991; Lopez et al., 1993).

The efficiency of the formulation may optionally also be demonstrated by the cellular immune response by detecting a "delayed-type hypersensitivity" (DTH) reaction in immunized animals. Finally, the immunomodulatory activity of the formulation is measured in animal tests.

Methods of Vaccinating a Subject

In another aspect, the present invention involves method of vaccinating a subject for influenza comprising: administering the disclosed cross-protective influenza vaccine to a subject in need thereof. The disclosed vaccine may be administered in a number of ways. For example, the disclosed vaccine can be administered intramuscularly, intranasally, or by microneedle in the skin. The compositions may be administered orally, intravenously, subcutaneously, transdermally (e.g., by microneedle), intraperitoneally, ophthalmically, vaginally, rectally, sublingually, or by inhalation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like.

Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 µg/kg to up to 100 mg/kg of body weight or more per vaccination, such as 10 µg/kg to 50 mg/kg, or 50 µg/kg to 10 mg/kg, depending on the factors mentioned above.

EXAMPLES

Example 1: HA3 Immunogen Evokes Broad HAI Titers in Horses

Figure 2:
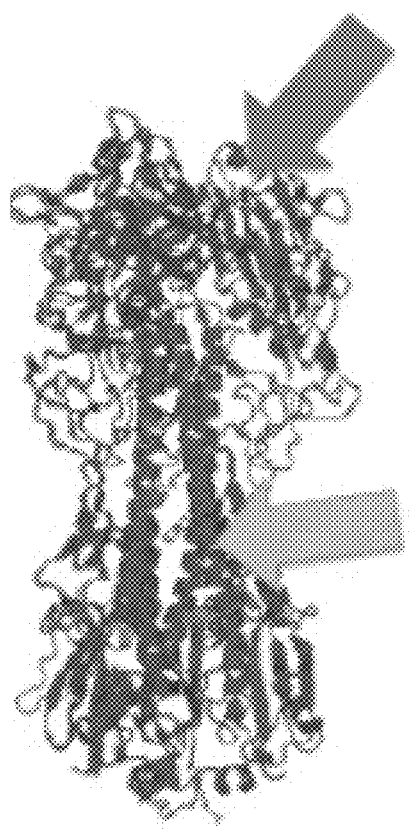
FIG. 2 shows the conformational structure of HA trimer. Typical vaccine approaches have targeted the HA2 stem region (green arrow) while equine HA3 antigen appears to elicit bnAbs to the HA head region (red arrow) as evidenced by HAI activity against multiple strains. HA was modeled from equine H3N8/Oregon/2013 using SWISS-Model.

Recent work by the inventors has uncovered an alternative approach to immunogen design that can elicit bnAbs by directing antibodies to multiple HAs. Utilizing a vaccine approach that targets the more variable HA head is not a typical approach to vaccination as most current research is investigating the HA stalk as a potential vaccine target (FIG. 2). As can be seen in Table 1, the Inventors have discovered that H3N8 LAIV elicits bnABs from mice that rival the vast majority of known bnAbs that arise naturally from infection of vaccine studies (monoclonals derived from H3N8 vaccinated mice show strong binding to diverse HAs).

TABLE 1

Summary of HA reactivity of H3Na sera vs. known bnAbs. Co5, 5J8, S139/1: Head Abs; CH65, CR6261: Head/Stem; CR8020, F10, CT149, 7A7: Stem Abs

| | Co5 | 5J8 | S139/1 | H3N8 Sera (Poly) | CH65 | CR6261 | CR8020 | F10 | CT149 | 7A7 |
|---|---|---|---|---|---|---|---|---|---|---|
| H1N1 | | | | | | | | | | |
| South Carolina/1/18 | + | + | NF | + | – | + | – | + | NF | NF |
| New Caledonia/20/99 | NF | + | NF | + | + | + | – | + | NF | NF |
| Brisbane/59/07 | | + | + (Weak) | + | + | + | – | + | NF | NF |
| California/07/09 | + | + | NF | + | – | + | – | NF | + | NF |
| Solomon Is/3/06 | NF | + | + | + | + | + | – | NF | + | NF |
| Beijing/262/95 | + | + | – | + | + | + | – | | + | NF |
| Moscow/10/99 | + | NF | NF | + | | + | – | NF | | |
| New Jersey/11/76 | NF | + | – | + | NF | NF | NF | NF | NF | NF |
| H3N2 | | | | | | | | | | |
| Shandong/9/93 | – | + | – | + | – | – | + | – | NF | NF |
| Perth/6/09 | + | + | + | + | – | – | + | | | |
| Brisbane/10/07 | + | + | + | + | – | – | + | – | + | + |
| HK/1/68 | + | + | – | + | – | + | + | NF | + | + |
| Bangkok/1/79 | – | NF | NF | + | – | – | + | – | NF | NF |
| Victoria/3/75 | – | | + | + | – | – | + | NF | NF | NF |
| Wisconsin/67/05 | NF | + | + | + | – | NF | NF | – | + | NF |
| H5N1 | | | | | | | | | | |
| Vietnam/1203/04 | NF | + | + | + | NF | + | – | + | NF | NF |
| H7N9 | | | | | | | | | | |
| Auhui/1/13 | NF | NF | NF | + | NF | NF | NF | NF | + | NF |
| H9 | | | | | | | | | | |
| HK/33982/99 | NF | NF | NF | + | NF | NF | NF | + | NF | NF |
| B Virus | – | – | – | – | – | – | – | – | – | – |

NF: No information found in literature

Figure 3A:
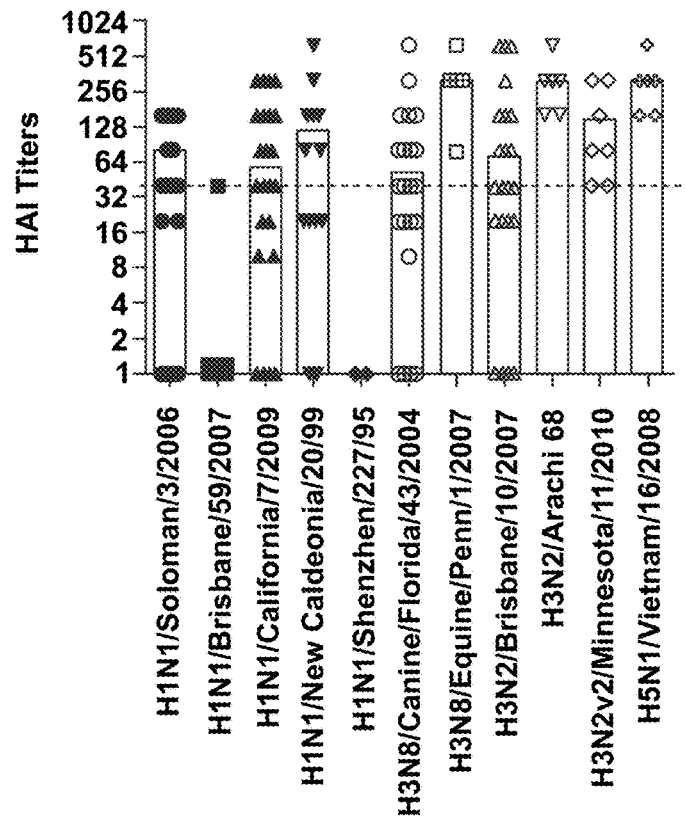
FIGS. 3A-B show H3N8 induces cross strain neutralization to human influenza strains. Sera from vaccinated horses were heat inactivated and RDE treated.
Figure 3B:
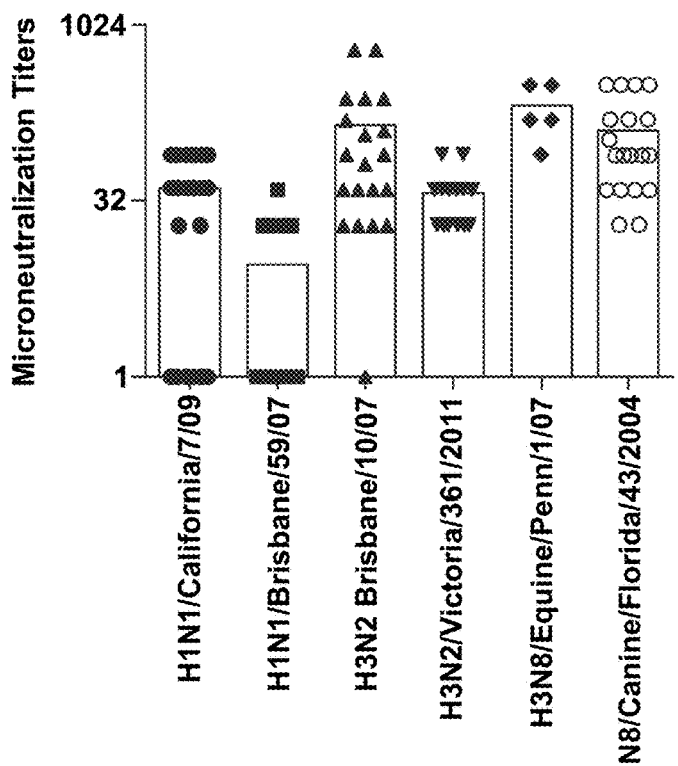

Serum for 2-5 year old horses were collected and tested for reactivity across multiple strains of influenza HA antigens. The HA3 immunogen derived from equine H3N8 virus invokes cross-strain protective HAI titers, such as human influenza A strains, in horses vaccinated with the live attenuated vaccine (FIG. 3). Significant HAI responses to many H3N2 viruses and H1N1 pnd09 strain were found (FIG. 3A). The same sera was then tested by microneutralization assay and found significant neutralization titers to multiple strains of influenza (FIG. 3B). HA3 immunogen vaccination drives Ig responses to multiple antigens in 2-5 year old horses. Furthermore, a survey of horse serum responses generated to H1N1 pnd09 infections show cross-strain protective HAI titers, while other recent work by the inventors also observed that this virus crossed the species divide and infect felines. Horses developed cross-strain (group) responses from the vaccine and not from infection (qRT-PCR of nasal swabs and serum against neuraminidase (NA) from H1N1 pnd09 were all negative). Other studies have determined that equine H3N8 vaccines can elicit protective HAI titers in multiple species (mice, horses, swine, and ferrets (45, 46)) but none have examined the cross-strain activity for use as a potential universal vaccine.

Figure 4:
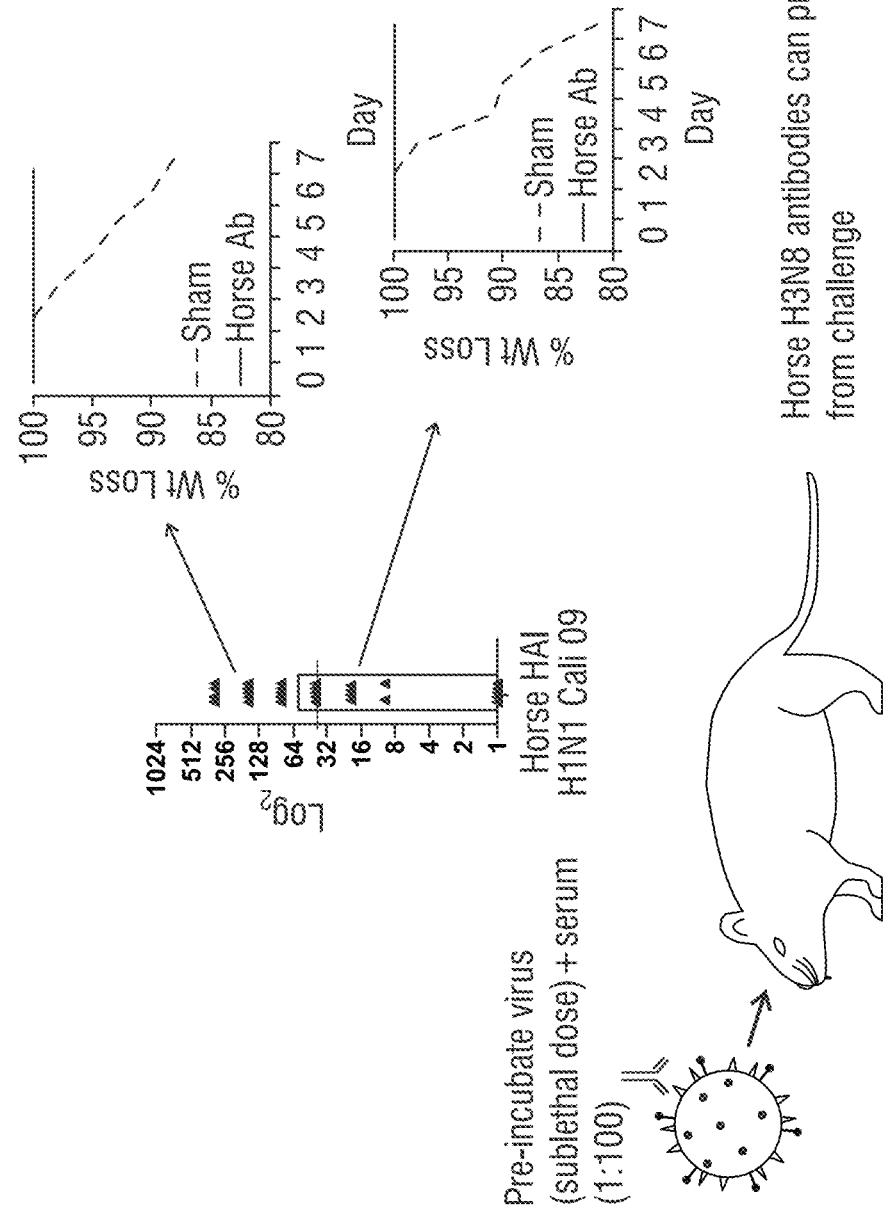
FIG. 4 shows equine HA antibodies drive protection from challenge in mice.

Next, the capacity of equine HA antibodies could drive protection in mice was investigated. Serum obtained from HA3 immunogen vaccinated horses was pre-incubated with a sub-lethal dose of H1N1 virus and compared to sham incubated H1N1 and subsequently used to challenge mice (FIG. 4). Interestingly, horse HA antibodies are capable of driving protection from challenge in mice. Together, these results provide a basis for the novel HA3 immunogen used as a vaccine as an alternative or in conjunction with future HA stalk vaccines in a universal influenza vaccine.

Example 2: Vaccination in Mice Leads to Antibodies to Multiple HA Antigens

Figure 5A:
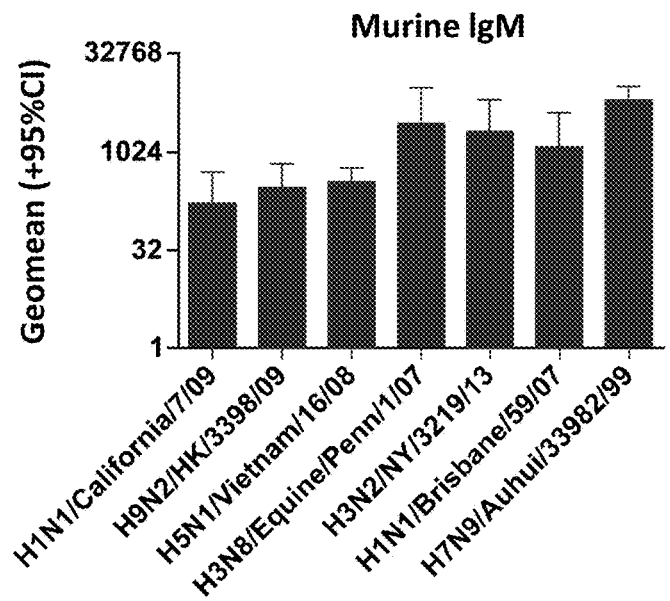
FIGS. 5A-C show H3N8 induces cross strain bnAb in mice similar to horses.
Figure 5B:
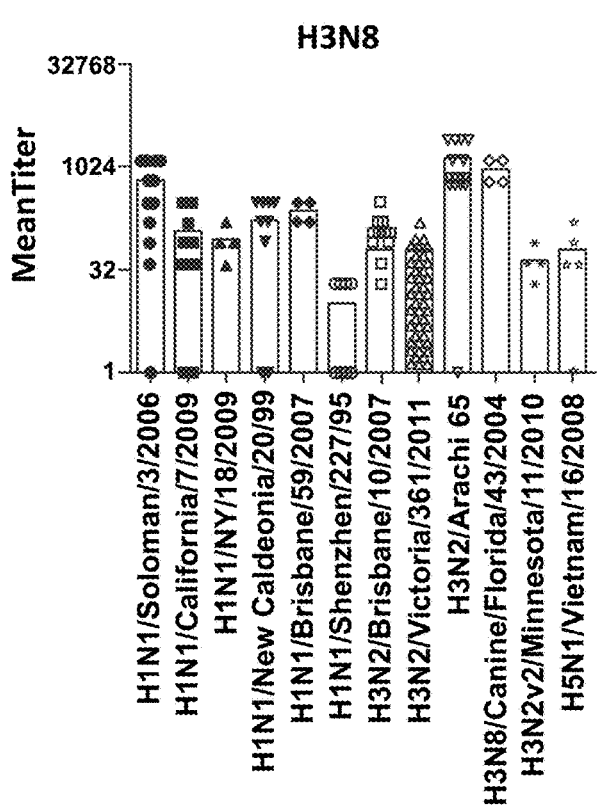
Figure 5C:
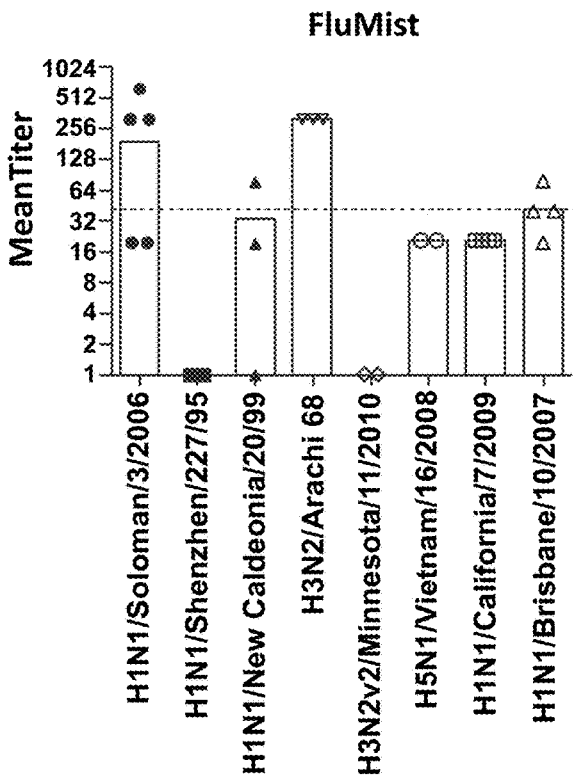

First mice were vaccinated by intranasal vaccination, using the live attenuated equine H3N8 vaccine (2014 stock, Merck) to determine whether mice could be infected in the nasal mucosal tract. However, no antibody responses were found suggesting that the mice were not susceptible to infection with the equine vaccine (data not shown). Next mice were vaccinated with the live H3N8 by intraperitoneal injections 2-3 times and tested their Ab responses to multiple influenza strains. Very high titers of Abs to whole H3N8 viruses were found and plated on ELISA microtiter plates (virions tend to split upon binding to the plates) suggesting that mice react to multiple viral proteins (data not shown). Next recombinant HAs were used (Beiresources, baculovirus expressed) for plating. It was found that mice reacted most strongly with multiple HA3 proteins, some reaction against H1 and H9 antigens, but a more limited reaction against H1N1 Brisbane 2007 HA antigen (FIG. 5). The data suggest that our immunization, although not optimized yet for HA dosages, could generate strong cross-reactive nAb responses across groups.

Figure 6:
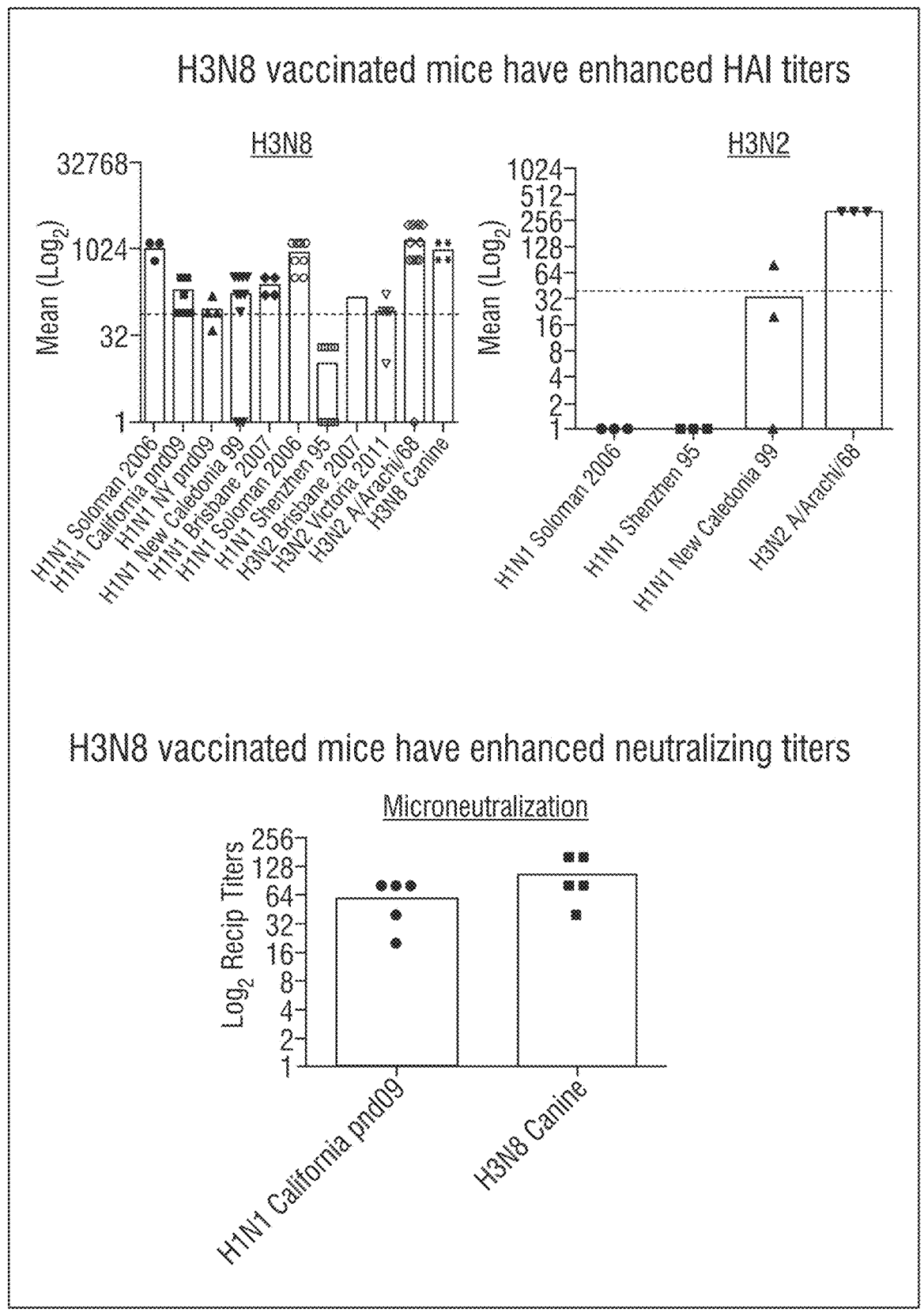
FIG. 6 shows H3N8 vaccinated mice develop cross strain HAI antibodies. Vaccinated Balb/c mice with H3N8 or killed H3N2 (X31) 2× (both 1600 HAU). Mice were bleed 4 weeks post-secondary vaccination and assayed for HAI or microneutralization activity.
Figure 7:
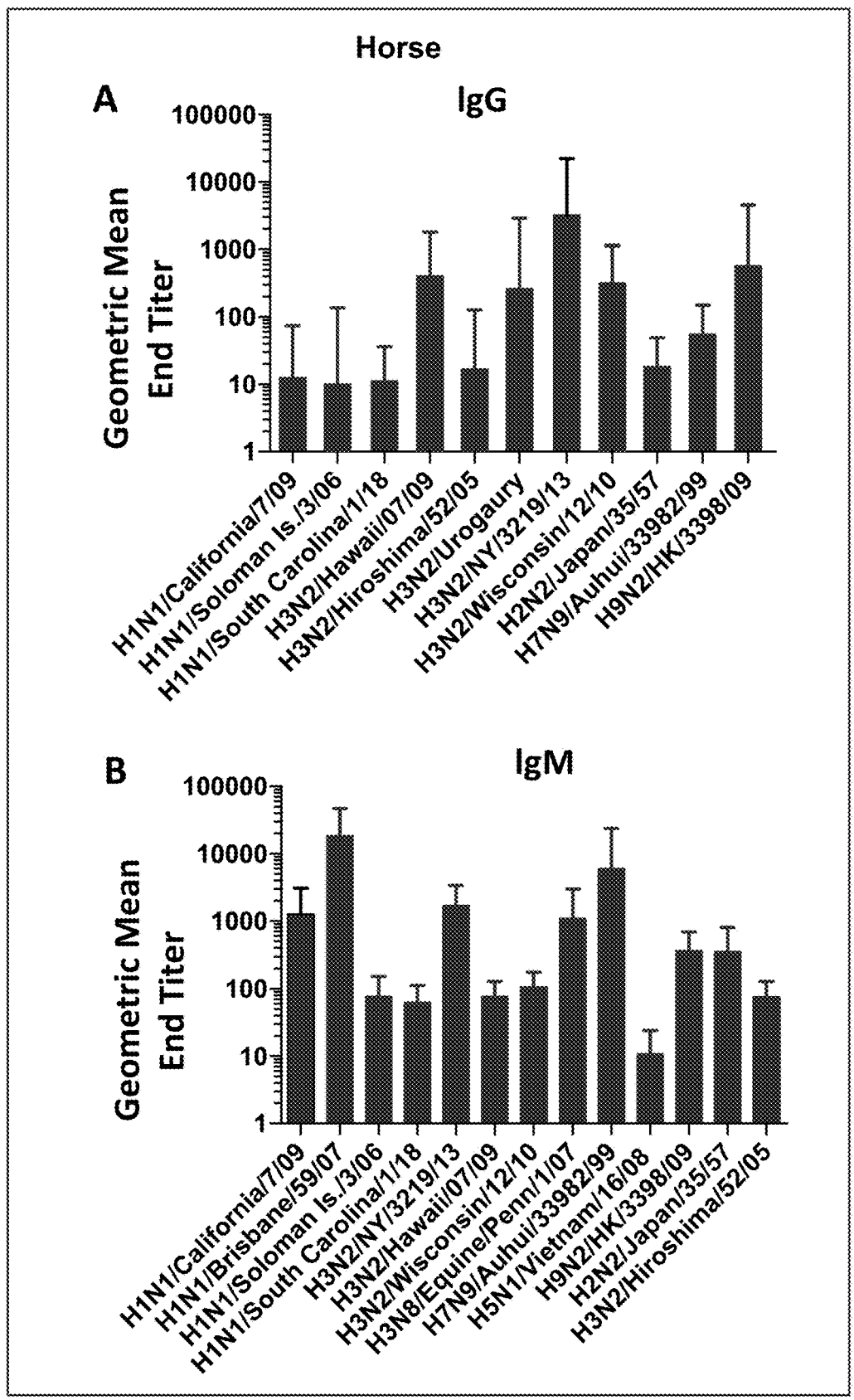
FIG. 7 shows H3N8 induces cross strain bnAb to human influenza strains. Sera from horses were reacted to recombinant HAs (CDC/ATCC) across multiple influenza groups with IgG or IgM end titers determined. Titer cutoff determined as 3×SD of the mean of the background.

Example 3: Mice Vaccinated With HA3 Immunogen Develop HAI/Microneutralization Antibodies Against Multiple Groups Mice were vaccinated with H3N8 again by intraperitoneal injections 2 times (without antigen optimization). Antibodies from the mice were isolated and tested using a HAI assay or by using a microneutralization across multiple strains. It was found that the vaccinated mice had significantly enhanced titers at or above 40 for most both assays (FIG. 6) that strongly mirrored those seen in horses (FIG. 3). Since our HAI titers were fairly comparable to our microneutralization titers, the data again strongly suggest that neutralization may be occurring predominately near the sialic acid binding site on the HA head. Since HAI activity against H1N1 Brisbane 07 and strong HAI against H1N1 pnd09 but no IgG responses against either recombinant protein derived from either virus (FIG. 5 and not shown) was detected, IgG versus IgM reactivity to a large number of recombinant HAs in horses and mice was investigated (FIG. 7). Strong binding across multiple viral groups (FIG. 7A-B) was found. These rHAs obtained from the CDC were not trimeric and thus we believe our titers might actually be lower than they should be given HA3 is capable of inducing nAbs that bind across the individual HAs in the timer.

Example 4: HA3 Immunogen Vaccinated Mice are Protected From Infection

Figure 8A:
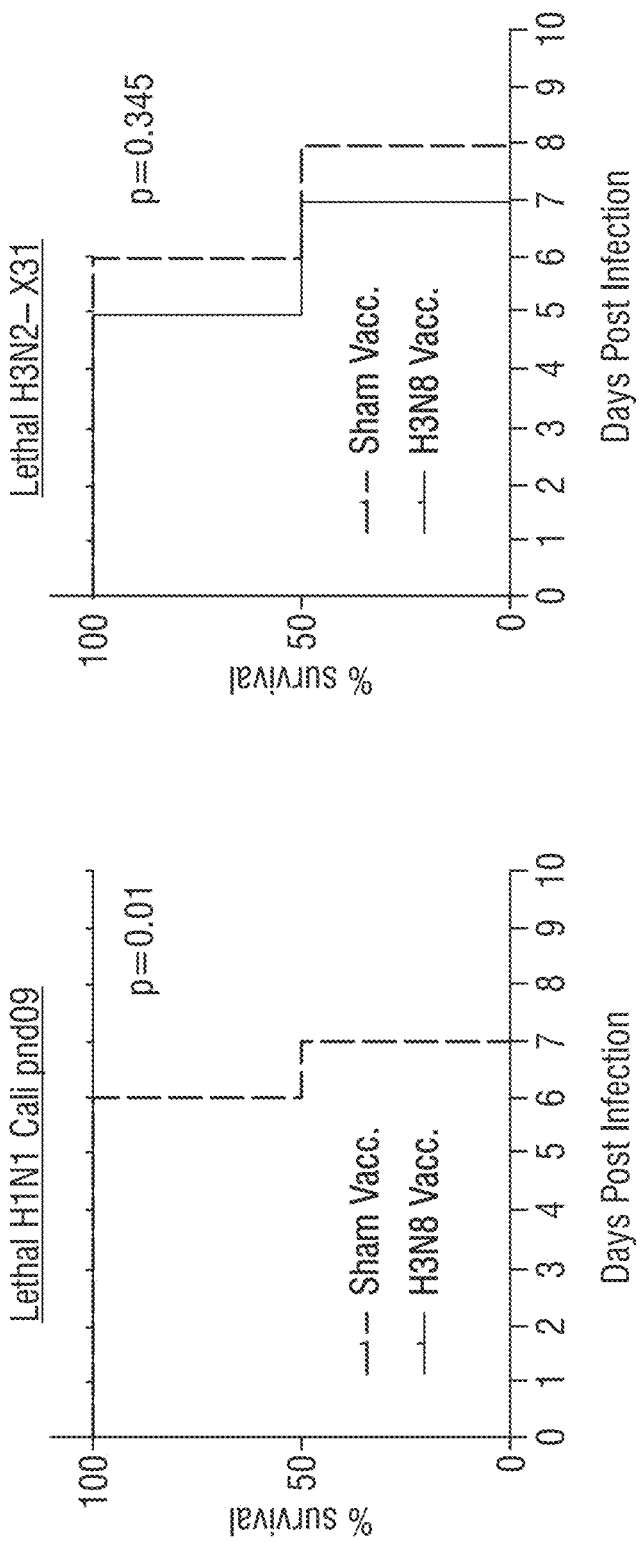
FIGS. 8A-C show H3N8 vaccinated mice are protected from challenge.

Mice were vaccinated with H3N8 or vaccinated with killed H3N2 (A/Arachi068, 107 TCID50) virus prior to being challenged. Using a lethal influenza A/California/pnd09 strain (reasserted with PR8), it was found that vaccinated mice were 100% protected from death (FIG. 8A) although weight loss suggested they were infected or exhibited strong immune responses (both can influence wt. loss in mice) (data not shown). Unvaccinated mice all died from infection. Using a lethal challenge (4 LD50) with A/Arachi/68/X31 virus, no vaccinated mouse was protected despite our previous data showing strong nAb titers across multiple HA3 antigens (FIG. 8A).

Figure 8B:
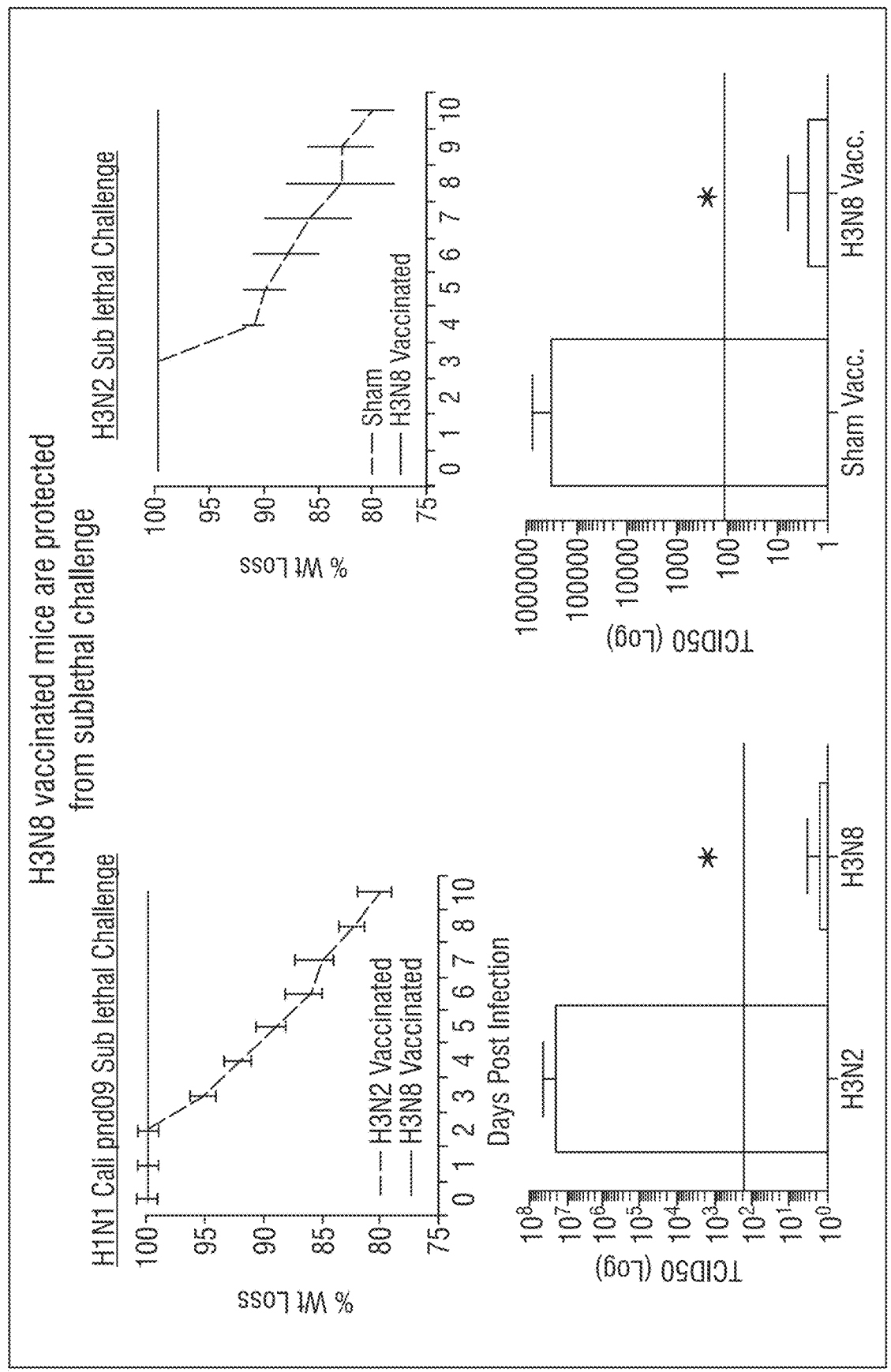
Figure 8C:
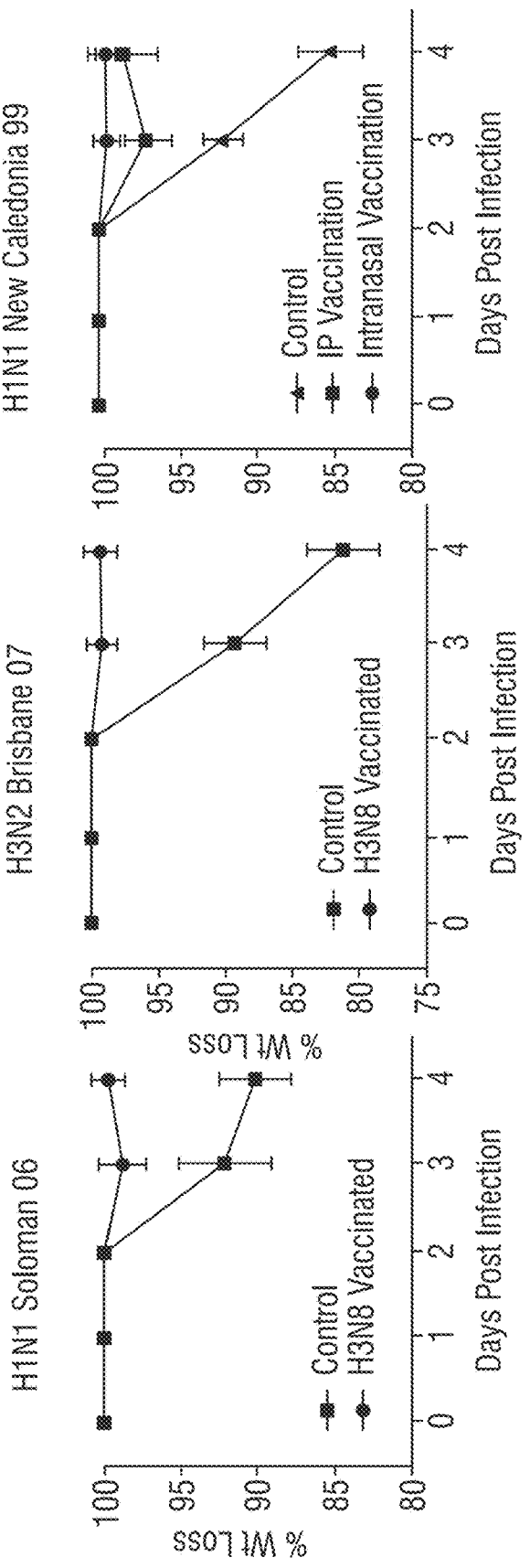

Interestingly, we next challenged both sets of vaccinated mice with a sublethal dosage of either H1N1 pnd09 (2,000 TCID50) or X31 (10,000 TCID50). In contrast to H3N2 vaccinated mice, no H3N8 vaccinated mouse was infected (lung viral burdens, not shown) or exhibited weight loss morbidity (FIG. 8B). Additional testing using H3N8 vaccinated mice challenged with H1N1 PR8 virus also reveal that mice are 100% protected from a sublethal challenge (data not shown) as well as from other H1N1 or H3N2 seasonal strains. Further testing using H1N1 pnd09 virus pre-incubated with serum derived from H3N8 vaccinated horses indicated complete protection from infection as well (no weight loss, viral titers in process, data not shown).

Example 5: Unique Conserved Epitopes are Exposed on HA3 Antigen Derived From H3N8

The discovery that vaccination using H3N8 led to nAb against H1N1 pnd09 but limited H1N1 Brisbane 2007 might be fortuitous for limiting our focus on protective epitopes. Although we know that HA3 viruses have many hidden protective epitopes, antibodies directed to those sites protect from other H3 challenge strains but not H1 strains.

Figure 9:
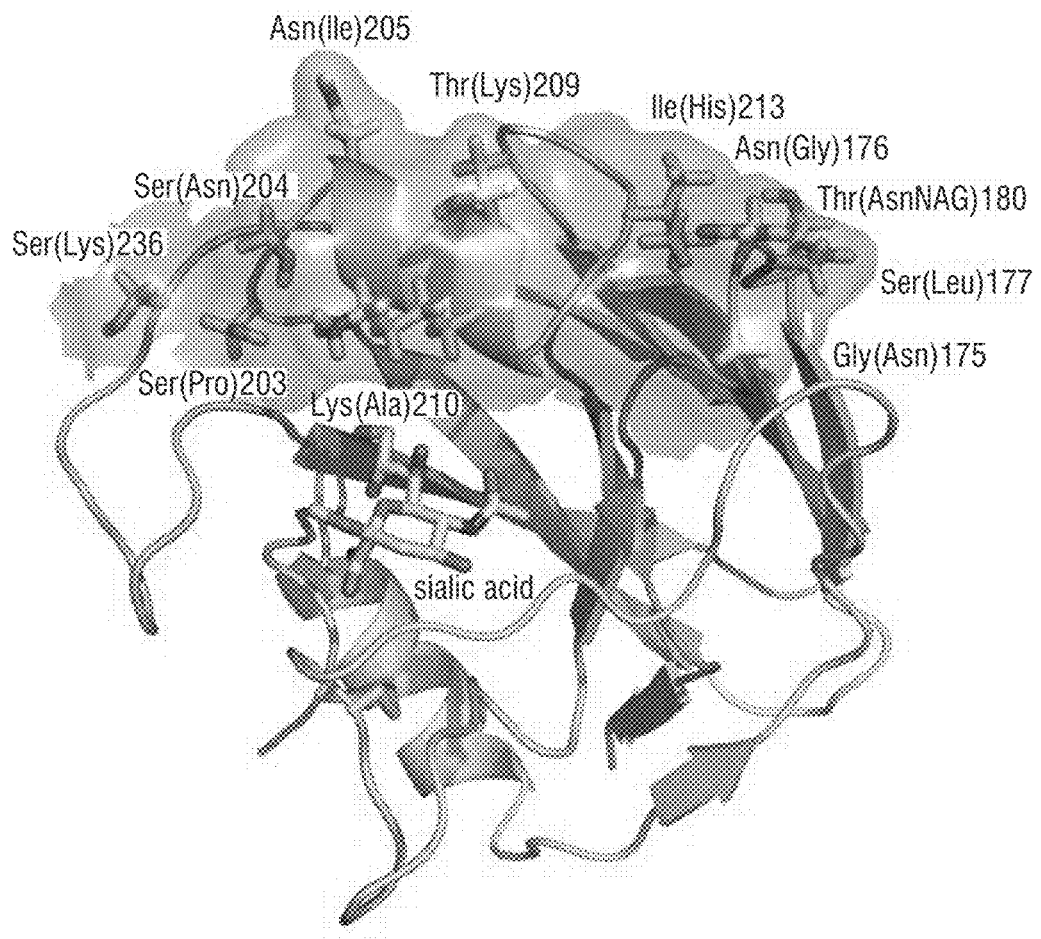
FIG. 9 shows a potential conformational epitope from equine HA3 was identified by sequence homology to the reactive human HA1 (strain A/California/04/2009) based on variants in the non-reactive human HA1 (strain A/Brisbane/59/2007). The epitope surface (grey shading) is map onto the homology model of equine HA3 (strain A/Xuzhou/01/2013) with amino acids numbered according to the full-length HA3 sequence and HA1 variants indicated in parenthesis. In addition to the HA1 (strain A/Brisbane/59/2007) sequence variants, a predicted glycosylation site at Asn180 may impair binding to this epitope. Antibody binding is expected to inhibit sialic acid binding. The location of the bound sialic acid is based on superposition with the known structure of HA1 (PDB ID: 1HGE) [1]. The homology model of equine H3 was calculated with the RosettaCM using structural templates of equine, canine and harbor seal HA3 structures (PDB IDs: 4UO0, 4UO4 and 4WA1) [2-4].

To facilitate our examination of key differences/similarities between equine HA3, Brisbane HA3, pnd09 HAL and Brisbane H1N1 HA1 antigens, we modeled each protein and examined for potential neutralization sites (FIG. 9). Of interest, we found a conserved region in the head of influenza strains that elicited nAbs that might be blocked by glycosylation (or partially) in the Brisbane 07 HA1 antigen. However, it is also possible that our immunogens need to elicit higher nAbs to that site to adequately bind to that region and neutralize Brisbane 07 H1N1 or there are additional neutralization sites our immunogen exposes. Furthermore, while both strains of H1N1 are very similar along linear epitopes there are additional nucleotides that differ that could also be targeted by nAbs. Furthermore, the previously described neutralization sites in HA3 antigen that allows for binding of HA antigens to form trimers could also be a site of nAb binding [32]. However, the R site (equine arg79, Asn80, Ser109, and Asp288) could be targeted but the L site looks too divergent to be protective. Furthermore, the stalk regions between H1N1 pnd09 and equine H3N8 HAs, like most group 1 versus group 2 viruses, appears too divergent to be the site of neutralization.

Figure 10:
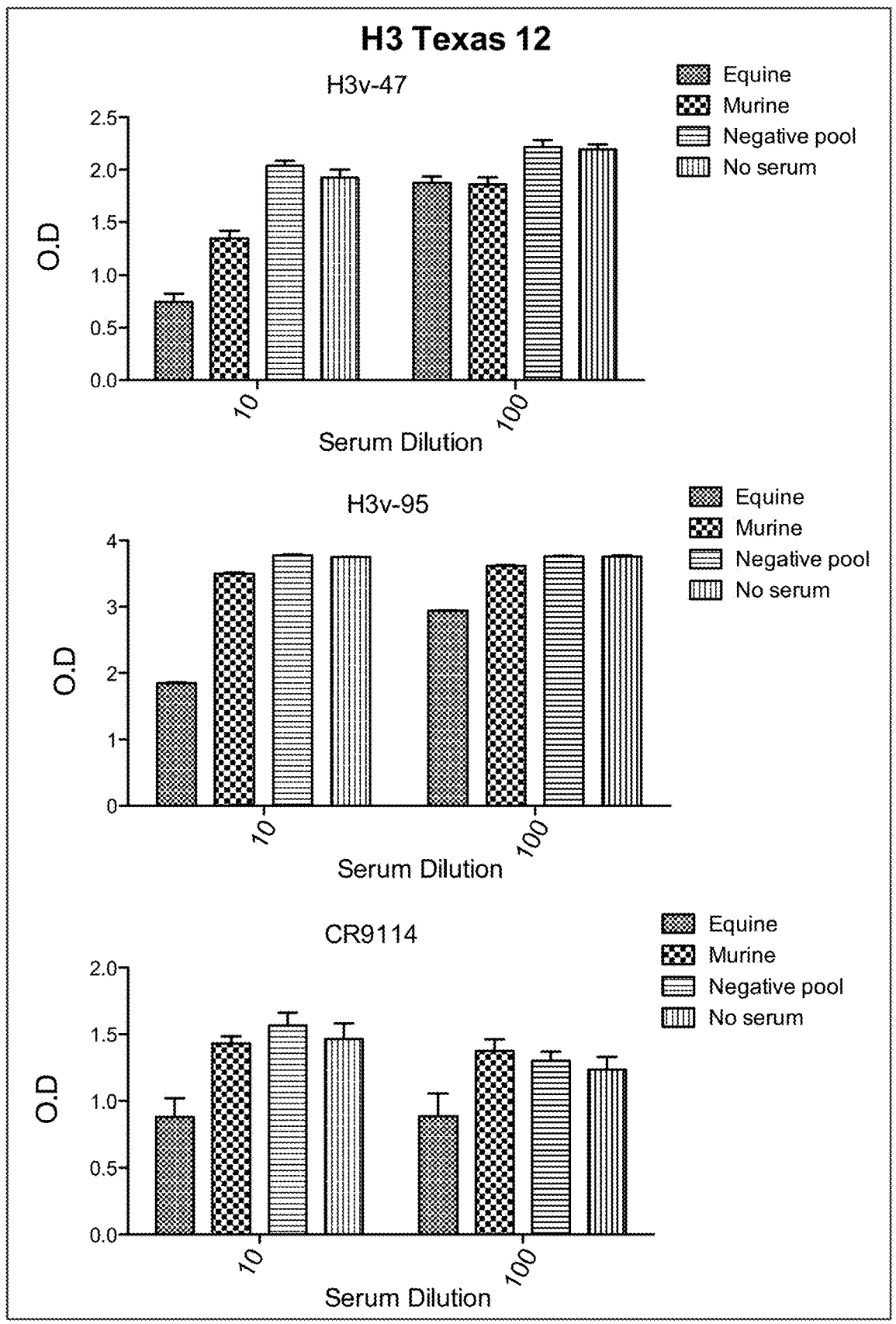
FIG. 10 shows competition assays suggesting sites of neutralization may be multiple. We preformed ELISA competition for antigen assays with pool vaccinated mouse or horse sera against panels of known bnAbs. We found that our sera competed with head binding (H3v-95) or esterase region (H3v-47) or even stem (CR9114) antibodies.
Figure 11:
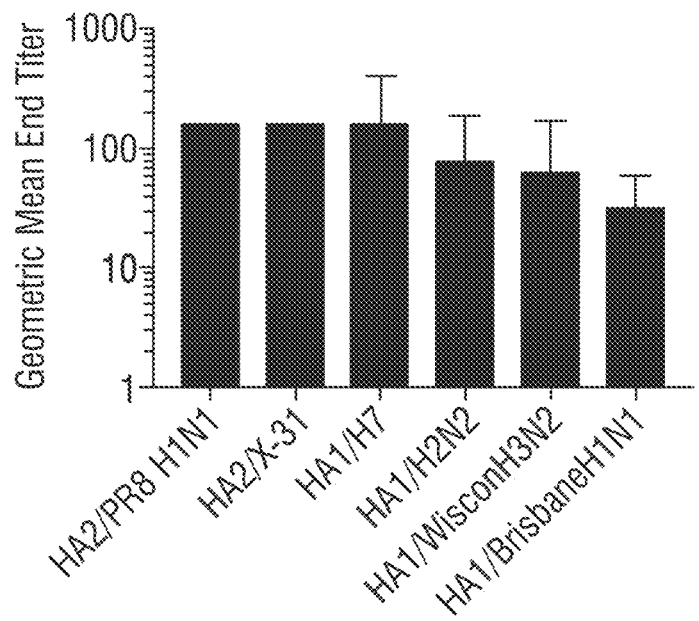
FIG. 11 shows sera from vaccinated mice shows binding to stem and head. We preformed ELISA for end pt. titers against headless HAs (sHA2) or recombinant HA1 portions of various rHAs. Anti-IgM was used for these studies.
Figure 12:
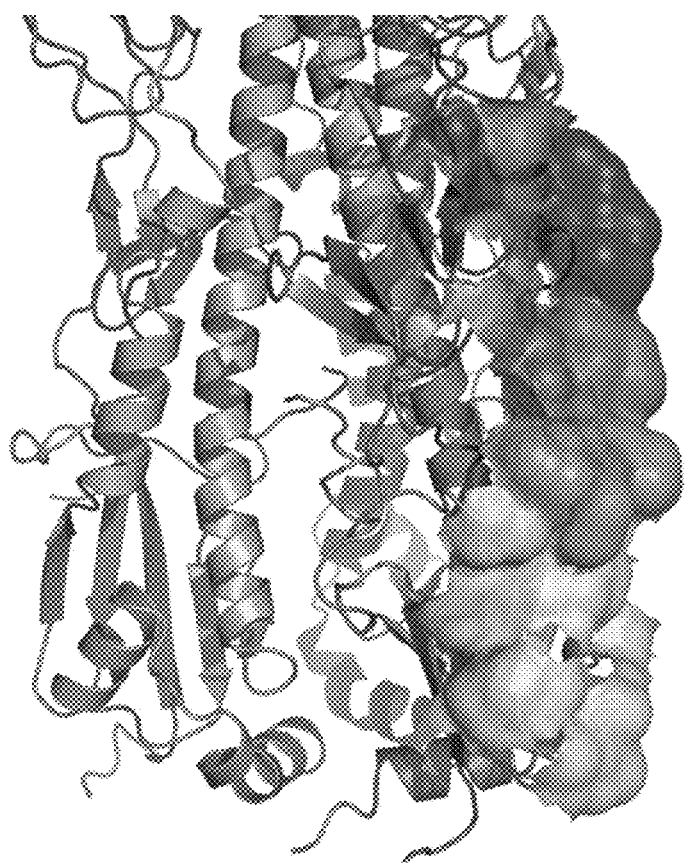
FIG. 12 shows potential binding site in the sHA2. There is overlapping stem epitopes for bnAbs C179 and CR6261, which bind to Group 1 HAs. There is considerable conservation between all HA strains within the HA2 portion of these epitopes, but not within the HA1 portion (particularly with the glycosylation site at Asn53 in equine/Kentucky/3/91/H3N8). Structural there is the possibility the get a cross-protomer epitope that includes the conserved HA2 and a neighboring HA1 beta hairpin across the trimer boundary. Sequence wise there is some conservation, but there is a glycosylation site in H1N1 strains at Asn40 that would block this site. It could also be similar to bnAb FI6v3 which has a similar epitope as CR6261, but is able to adapt to the glycosylation site at Asn53 in H3 strains and minimizes interactions with the HA1 parts of the epitope (in particular there is almost no contact with the Asp306-Lys307-Pro308 loop, numbering from equine Kentucky H3N8). The other pan-serotypic antibody CR9114 appears to binding similar to FI6v3 and also accommodates the Asn53 glycosylation site. So, if the binding we see is not due to multiple bindings sites from more than 1 bnAbs, then an epitope that overlaps CR6261 is possible and the antibody could adapt to strain variations and glycosylation. purple—HA head, green—sHA2, red—overlapping epitope surface of C179 and CR6261, pink—C179 only, blue—CR6261 only, yellow—CR8020 only, orange—overlap between all three antibody epitopes. Fl6v3 10 is exceptionally broadly binding as are the preliminary screens of the H3N8 antibodies (see table 1) under study.

Competition assays suggest at least 3 individual bnAbs are elicited after vaccination. We vaccinated (and boosted) mice and horses with our vaccine 1 (horses) to 3 times (mice) and examined potential sites of neutralization by using a competition assay with a panel of known bnAbs. Of interest, we found no competition with 5J8 a bnAb for H1N1 but did find competition with Hw-95 a bnAb for H3N2 viruses. However, Hw-95 does not bind H1N1. This suggests that our antibody neutralizes in the head region and that some of the neutralization site might overlap with H3v-95. We also found competition with H3v-47, which is known to bind to the esterase region in a known broadly neutralizing epitope. Both of these bnAbs (H3v-47/95) neutralize H3N2v2 viruses that crossed from swine into humans. Finally, we found that our antibody competed with CR1995 which binds and neutralizes the HA stem region and we have further confirmation that our antibodies bind to headless HAs derived from H1N1 and H3N2 viruses ((FIG. 10, 11). Based on these data, we hypothesize we may have stem bnAbs and generated another prediction model for neutralization (FIG. 12). Importantly CR9114 does not neutralize H1N1 but our vaccine induces stem antibodies (data not shown). Thus, our antibodies, like the head binding, may be in a similar site but not the exact site as the bnAb were tested against.

Figure 14:
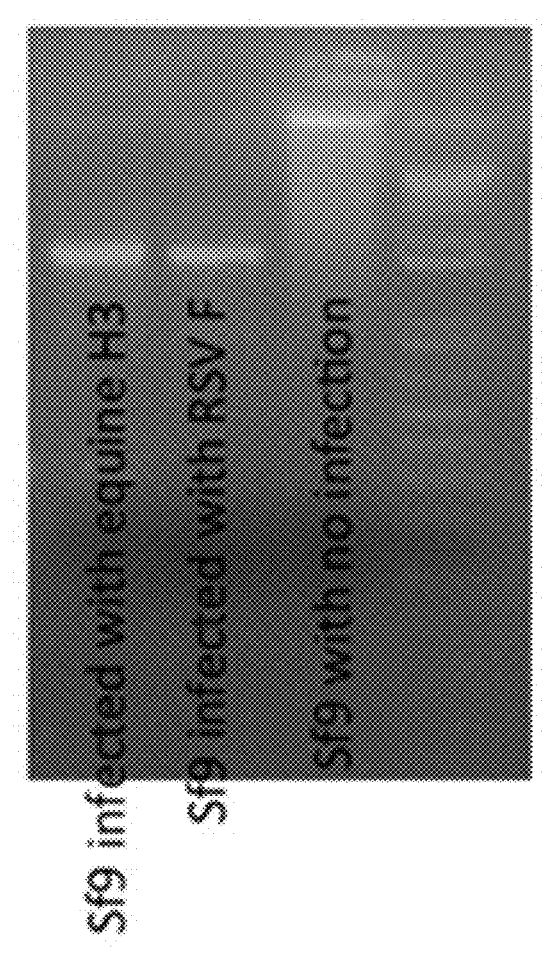

Example 6: Construction of Recombinant Equine HA3 and a Comparator H3N2 Texas/2012 HA for Vaccination and Antibody Binding Studies We initially generated HA eukaryotic expression vectors for generating recombinant HA in 293T cells but found very low yield of the HA and high bacterial toxicity in E coli carrying the plasmid. Thus, we switched to using the baculovirus system and generated a recombinant trimeric HA using a foldon domain and histidine tag placed behind the full HA protein. We detected limited expression of the protein using this system, despite high baculovirus titers, and have changed to a baculovirus system that stabilizes toxic or unstable proteins (MirusBio). We have also generated another HA plasmid that is codon optimized for Sf9 cells and generates secreted HA to make purification easier. The recombinant baculovirus has been generated (FIG. 14).

Example 7: Identification of Monoclonal Antibodies That Neutralize Broadly From Vaccinated Mice We vaccinated mice with 2 doses of our vaccine followed by a booster 5 days prior to harvest of their spleens. The spleenocytes were pooled and fused to Sp2/0 myeloma cells that stably make murine IL-6. We generated over 1000 clones and screened for dual reactivity against recombinant H1 and H3 proteins. We have subsequently identified 3 of those clones that are reactivity against H1N1 pnd09, H1N1

Solomon/03/06, H3N2 Wisconsin, H3N2 Victoria, and H3N2 Hawaii. Further testing of 1 of these clones indicated HAI activity against multiple H1 and H3 viruses (Table 2).

TABLE 2

Clone: 27-10 F8 HAI Testing

| H3N2 | H1N1 |
|---|---|
| Mississippi/1/85 + | New Jersey/11/76 + |
| Shangdong/9/93 ++ | California/7/09 +++ |
| Perth/16/09 ++ | Solomon Is./3/06 +++ |
| Wisconsin/67/05 ++++ | New Caledonia/20/99 + |
| Minnesota/11/10 v2 ++ | |

Neutralized virus . . . + indicate level of HAI in comparison to other viruses tested. Original titers were low and are undergoing boosting by hybridoma selection

Example 8: Testing of LAIV Against H1 and H3 Challenge Viruses Using Adjuvants We have previously determined that vaccinated horses or mice produce primarily IgM that cross reacts to multiple influenza HA strains. We next sought whether we could convert more of the IgM into IgG or induce higher levels of cross-reactive B cells in the lungs.

Figure 15:
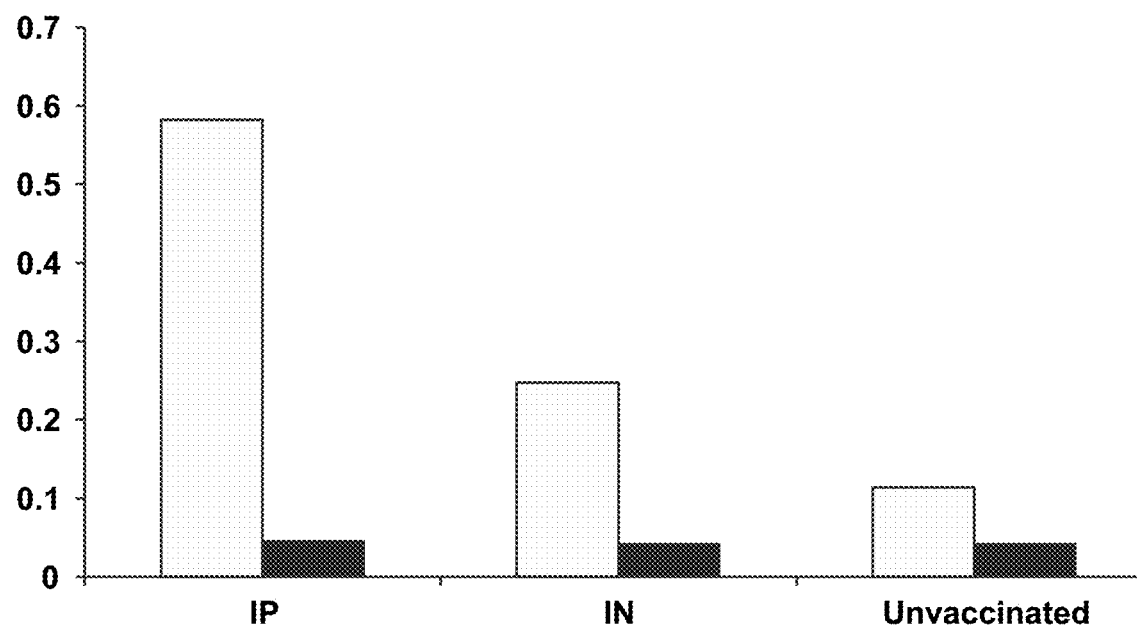
FIG. 15 shows serum response of vaccinated mice after inclusion of Alum adjuvant. We assessed serum reactivity after vaccination using IP versus IN route using LAIV with Alum adjuvant against rHA from H1N1 Solomon Is./3/06. Data is from a representative animal from each group. Blue bars are with Alum and red bars are without alum. Not shown is that IP induced higher numbers of reactive B-cells by ELISPOT assay.
Figure 16A:
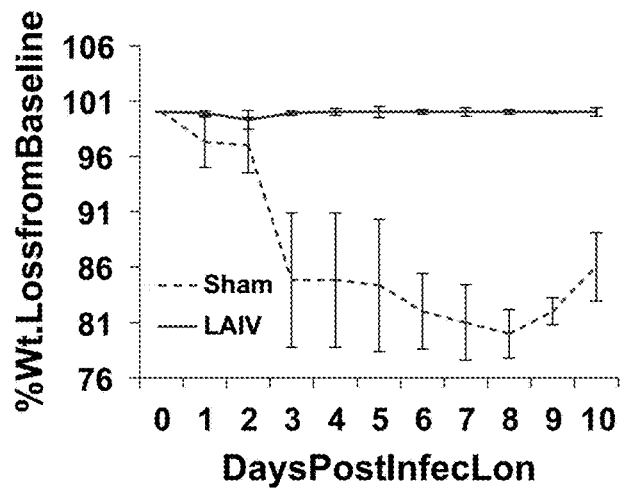
FIGS. 16A-C show vaccination with LAIV containing Alum leads to better morbidity or survival than sham.
Figure 16B:
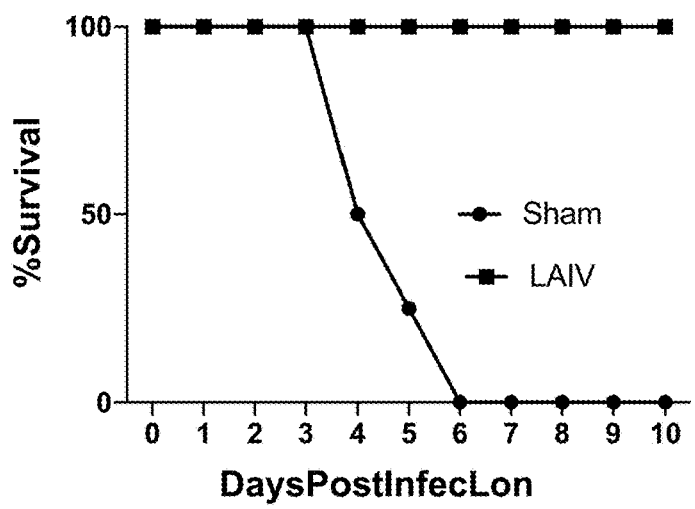
Figure 16C:
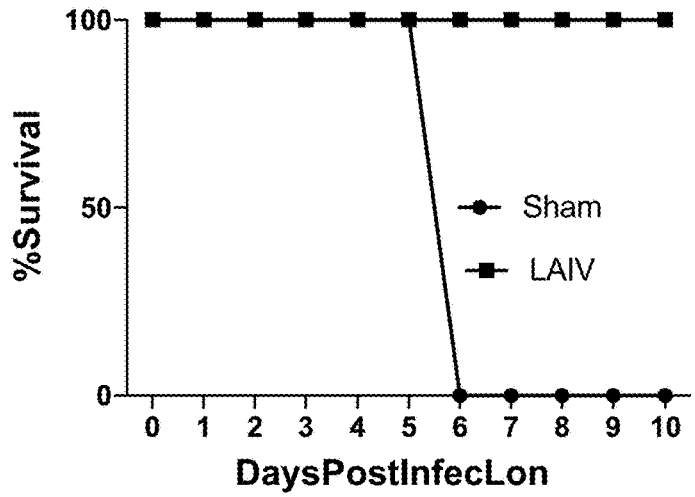

To facilitate this, we choose to test inclusion of Alum adjuvant at 0.1 mg/vaccine dosage (Alhydrogel, Invivogen). We chose Alum given its ability to boost serum Ig titers and also due to its safety and approval by the FDA in vaccines for humans. This dosage was the minimum dosage suggested by the manufacturer. Of interest, inclusion of Alum into our formulation (LAIV viral stocks) not only led to higher total cross-reactive Ig but also caused enhanced lung residency of vaccine specific (and cross-reactive) B-cells and caused a higher titer of IgG than the typical IgM predominance without Alum we have observed (FIG. 15). The vaccine was administered by IP injection given the volume restrictions for intramuscular injections in mice.
Testing of LAIV Against H1 and H3 Challenge Viruses Using Adjuvants We have previously examined protection afforded by the vaccine after two doses without Alum. Here, we examined the level of protection afforded after challenge with H1 and H3 viruses in mice vaccinated with LAIV containing Alum. As shown in FIG. 16, LAIV vaccinated mice were protected from challenge viruses (sublethal or lethal) and these further suggest this vaccine could provide universal protection against seasonal influenza infections. Serum reactivity against H5, H7 and H9 suggest further protection might be possible against pandemic strains as well.

Example 9: Additional Hybridoma Clones Isolated That are IgG Isotypes

We previously have obtained cross-reactive IgM hybridoma clones from vaccinated mice after fusion of spleenocytes to Sp2/mIL6 myeloma cells. However, inclusion of IgM in our crystallization imagining studies of antibody/antigen complexes could prove somewhat difficult given antibody affinity and size and thus we sought to determine whether we could isolate IgG specific cross-reactive clones from our LAIV/Alum vaccinated mice. Specifically, we used 2 vaccine dosages followed by a boost using recombinant HA three days prior to spleen harvest. Of 660 wells of cell fusions, we have identified 6 unique clones that bind to multiple recombinant H1 and H3 antigens and that are IgG isotype. We are currently expanding these hybridomas and further characterizing them for use in crystallization studies and neutralization studies. B cell clones will also be sequenced in the CDR3 region and compared to our IgM clones to determine they are derived from the same reactive B cell pools or are unique from each other.

Example 10: Testing rHA Against LAIV and H3/H1 Vaccines

Figure 17:
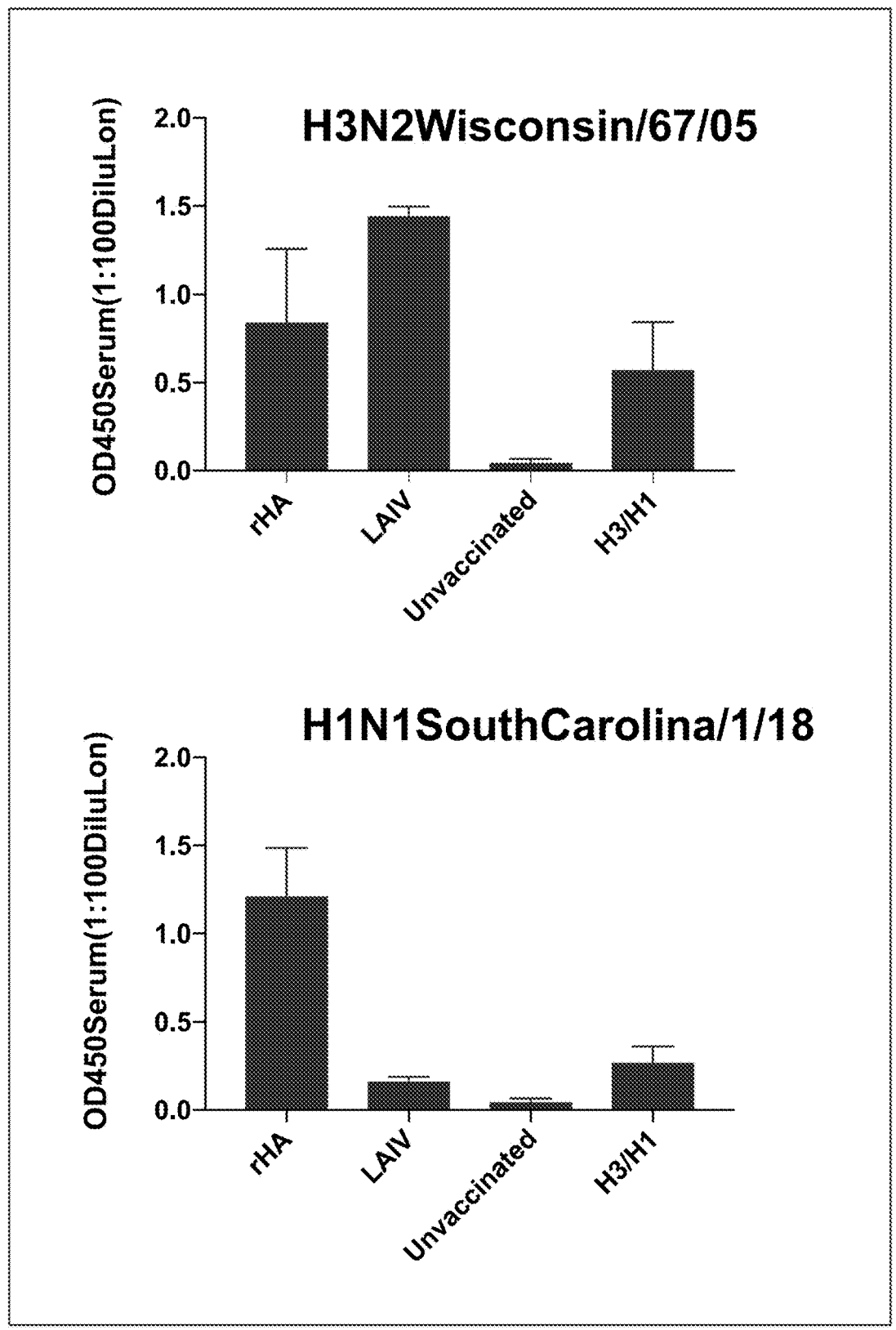
FIG. 17 shows rHA vaccination shows strong reactivity to H3 and H1 antigens. We vaccinated mice with rHA (800 HAU), LAIV (1600 HAU), Sham (BSA), or a mix of California H3N2/14 and H1N1/09 cold adapted viruses and assessed serum reactivity after 1 vaccination. All vaccinations contained Alum adjuvant. These data suggest rHA may induce similar efficacious serum responses as LAIV. (n=5 each group).

We have previously demonstrated we have constructed recombinant HA based on the equine influenza strain of H3N8 Kentucky/1991 using overlapping oligo synthesis and cloning into a baculoviral expression system. The rHA is induced in a trimer formation using a foldon domain and is cleaved by trypsin on a nickel resin column into active HA. We began efficacy testing of the recombinant HA (800 HAU) against LAIV (1600 HAU) with Alum at the concentration previously discussed. After one dosage, we found similar levels of cross-reactive IgG in both rHA and LAIV against H1 antigens and slightly higher responses to H3 in LAIV vaccinees. After two dosages, we found these trends continued. We next examined the HAI titers across both vaccine groups and found similar functional titers. FIG. 17 shows the data for this analysis. We have now obtained higher yield baculoviral expressed rHA for vaccination using higher protein concentration similar to our LAIV studies.

We next vaccinated mice with rHA, LAIV, an equal mix of cold adapted California H1/2009 and California H3/2014, or PBS sham with 9 µg of BSA. All mice received two dosages containing equal amounts of Alum adjuvant. Mice were then challenged with a 40LD50 dosage of H1N1 New Jersey/1976 (reassortment strain with H1N1 PR/8/34 for infection in mice). Of interest, all sham vaccinated mice died at 6 days post-infection. While the mixed H1/H3 vaccinees all survived infection, they lost more weight and took longer to recover than LAIV vaccinated mice. Of further interest, the rHA mice also all survived challenge but had equivalent weight loss after lethal challenge as LAIV.

Figure 18:
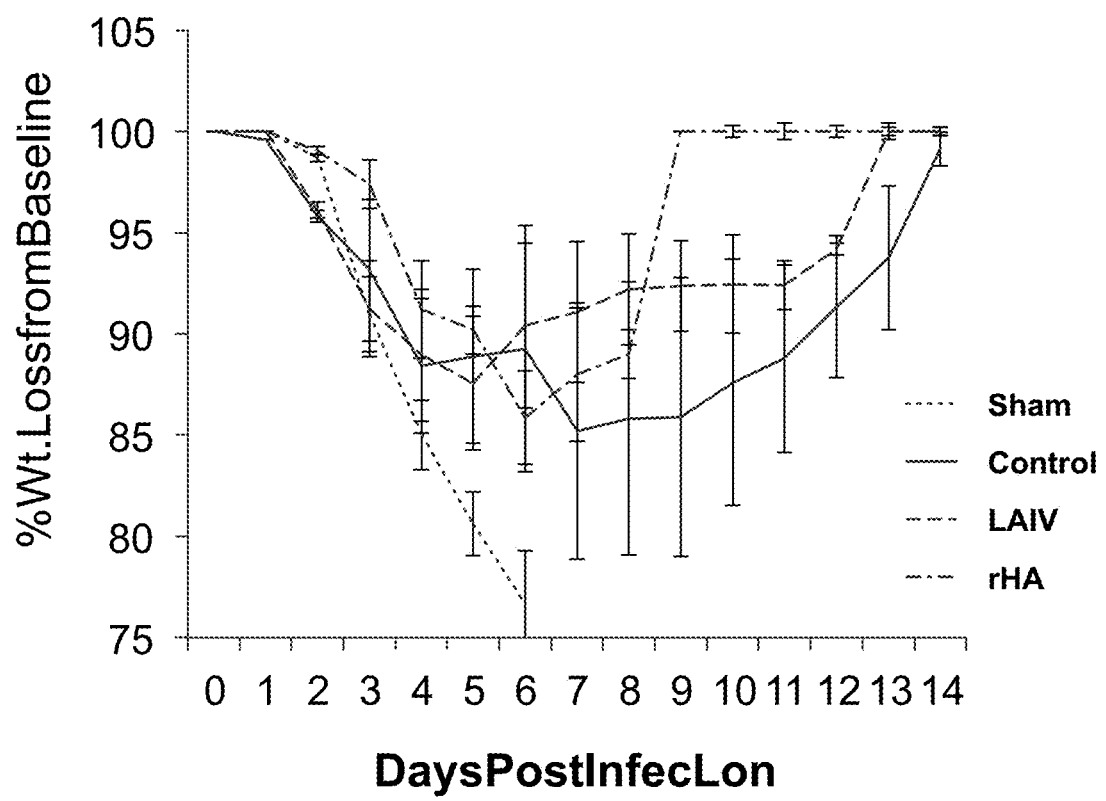
FIG. 18 shows rHA vaccination demonstrates protection from stems from HA antibody neutralization. We vaccinated mice with rHA (800 HAU), LAIV (1600 HAU), Sham (BSA), or a mix of California H3N2/14 and H1N1/09 cold adapted viruses and assessed weight loss and survival after 40 LD50 dosage of H1N1 New Jersey/8/76 (swine pandemic virus crossed to internal PR8 proteins). All sham vaccinated mice died at day 6 post-infection. H1N1 NJ/76 vaccination is known to confer protection from H1N1 Cali/09 and SC/1918 pandemic challenges and thus likely Cali/09 also protects from NJ/76 challenge. The rHA or LAIV protected just as well if not better than the Cali H1/H3 mix of viruses.

These data are especially important as both LAIV and H1/H3 cold adaptive viruses induce anti-NP specific CD8 T-cells while M2 cross-reactive broadly neutralizing antibodies are routinely generated by intact viruses in mice. rHA antigen does not have these and thus the data further confirm that that the protection afforded by equine HA3 is by broadly neutralizing antibodies to the HA protein. See FIG. 18 for the challenge data.

Example 11: Additional Efficacy Testing in Chickens

Prior to vaccinating in ferrets, we sought to determine whether the vaccine could induce protection in vaccinated chickens with a concentration on high pathology viral strains (HPAI, e.g. H5, H7, and H9 viruses). Vaccination in chickens could be important as cross-species infection of these potential pandemic strains of virus is ongoing especially in Asia. Thus, we vaccinated Leghorn chicks by intramuscular injection (with Alum) twice and examined the cross-reactivity of sera and HAI titers to HPAI. We found that vaccinated chickens were induced to make cross-strain antibodies to H1, H3, H5, and H7 recombinant HA antigens.

Figure 19:
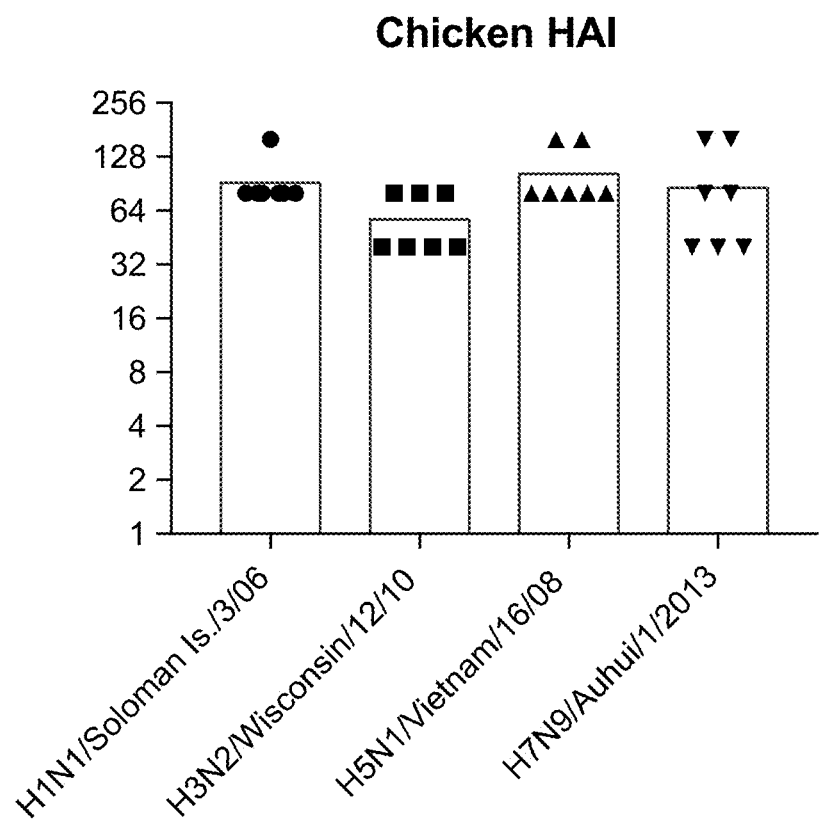
FIG. 19 shows LAIV vaccination with Alum confers HAI titers against highly pathogenic influenza strains. We vaccinated leghorn chickens with LAIV containing Alum or with PBS/BSA/Alum 2× before assessing their serum HAI titers. We found all vaccinated chickens had higher than protective titers against many HPAI viruses. Not shown is sham had no protective titers after vaccination.

Furthermore, we found that vaccination of chickens induced protective HAI titers to H5 viruses and H7 viruses (chemically inactivated strains). However, we believe that the amount of Alum or use of this adjuvant rather than mineral oil was not optimized yet for this species as the antibody profile of the response appeared more like our prior results in mice without Alum antigen (e.g. IgM dominant response rather than IgY (chicken IgG)). Nonetheless, this vaccine has the potential for use in chickens to prevent the potential spread of pandemic strains of influenza into the human population and further supports efficacious protection in yet another species. See FIG. 19 for HAI data.

Example 13: SEQUENCES

```
source
1..1725
/organism = "Influenza A virus (A/equine/Kentucky/4/1980(H3N8))"
/mol_type = "viral cRNA"
/strain = "A/equine/Kentucky/4/1980"
/serotype = "H3N8"
/host = "Equine"
/db_xref = "taxon: 475462"
/segment = "4"
/country = "USA: Kentucky"
/collection_date = "1980"

gene
11..1708
/gene = "HA"

CDS
11..1708
/gene = "HA"
/function = "receptor binding and fusion protein"
/codon_start = 1
/product = "hemagglutinin"
/protein_id  "ABY81448.1"

/translation = "MKTIIILILLLTHWVYSQNPTSGNNTATLCLGHHAVANGTLVKTI

TDGQIEVTNATELVQSTSIGKICNNPYRVLDGRNCTLIDAMLGDPHCDVFQYENWDLF

IERSSAFSNCYPYDIPDYASLRSIVASSGTLEFTAEGFIWTGVTQNGRSGACRRGSAD

SFFSRLNWLTKSGNSYPTLNVTMPNNNNFDKLYIWGIHHPSTNNEQTKLYIQESGRVT

VSTKRSQQTIIPNIGSRPWVRGQSGRISIYWTIVKPGDILMINSNGNLVAPRGYFKMR

TGKSSVMRSDAPIDTCVSECITPNGSIPNDKPFQNVNKVTYGKCPKYIKQNTLKLATG

MRNVPEKQIRGIFGAIAGFIENGWEGMVDGWYGFRYQNSEGTGQAADLKSTQAAIDQI

NGKLNRVIERTNEKFHQIEKEFSEVEGRIQDLEKYVEDTKIDLWSYNAELLVALENQH

TIDLTDAEMNKLFEKTRRQLRENAEDMGGGCFKIYHKCDNACIGSIRNGTYDHYIYRD

EALNNRFQIKGVELKSGYKDWILWISFAISCFLICVVLLFIMWACQKGNIRCNICI"

sig_peptide
11..58
/gene = "HA"

mat_peptide
59..1042
/gene = "HA"
/product = "HA1"

mat_peptide
1043..1705
/gene = "HA"
/product = "HA2"

ORIGIN
    1  tctgtcaatc atgaagacaa tcattatttt gatactactg acccattggg tctacagtca
   61  aaacccaacc agtggcaaca acacagccac actatgtctg ggacaccatg cagtagcaaa
  121  tggaacattg gtaaaaacaa taactgatgg ccaaattgag gtgacaaatg ctactgaatt
  181  agttcagagc acttcaatag ggaaaatatg caacaaccca tatagggttc tagatggaag
  241  aaactgcaca ttaatagatg caatgctagg agatccccac tgtgatgttt ttcagtatga
  301  gaattgggac ctcttcatag aagaagcag cgctttcagc aattgctacc catatgacat
  361  ccctgactat gcatcgctcc ggtctattgt ggcatcttca ggaacattag aattcacagc
  421  agagggattc atatggacag gtgtcactca aaacggaaga agtggagcct gcagaagggg
  481  atcagccgat agtttcttta gccgactgaa ttggctaaca aaatctggaa attcttaccc
  541  cacgttgaat gtgacaatgc ctaacaataa caatttcgat aaactataca tctggggat
```

```
601  ccatcacccg agcacaaaca atgagcagac aaaattgtat atccaagaat cagggcgagt 661  aacagtctca acaaaaagaa gtcaacaaac aataatcccc aacatcggat ctagaccgtg 721  ggtcaggggt caatcaggca ggataagcat atattggacc attgtgaaac ctggagatat 781  cctaatgata aacagtaatg gcaacttagt tgcaccgcgg ggatatttca aaatgcggac 841  agggaaaagc tctgtaatga gatcagatgc acccatagac acttgtgtgt ccgagtgtat 901  tacaccaaat ggaagcatcc ccaacgacaa accatttcaa aatgtgaaca aagttacata 961  tggaaaatgc cccaagtata tcaagcagaa tactttgaag ctggccactg ggatgaggaa 1021 tgtaccagaa aagcaaatca gaggaatctt tggagcaata gcgggattca tagaaaacgg 1081 ctgggaagga atggttgatg ggtggtatgg attccgatat cagaattcgg aaggaacagg 1141 acaagctgca gatctaaaga gcactcaagc agccatcgac cagatcaatg gaaaattgaa 1201 cagagtgatt gagaggacca atgagaaatt ccatcaaata gagaaggaat tctcagaagt 1261 ggaagggaga atccaggact tggagaagta tgtagaagac accaaaatag acctatggtc 1321 ctacaatgca gaattactgg tggctctaga aaatcaacat acgattgact taacagatgc 1381 agagatgaat aaattattcg aaaagactag gcgccagtta agagaaaacg cggaagacat 1441 gggggggtgga tgtttcaaga tttatcacaa atgtgataat gcatgcattg gatcaataag 1501 aaatgggaca tatgaccatt acatatacag agatgaagca ttaaacaacc gatttcaaat 1561 taaaggtgtt gagttgaaat caggctacaa agattggata ctgtggattt cattcgccat 1621 atcatgcttc ttaatttgcg ttgttctatt gggtttcatc atgtgggctt gccaaaaagg 1681 caatatcaga tgcaacattt gcatttgagt aaactgatag ttaaa
```

Example 14: Divergent Differences in Equine HA Antigen

While equine HA has 95-98% homology between all strains, there are some key differences that might make one more of an ideal immunogen. We compared equine Georgia/81 with our immunogen and found key differences in amino acid substitutions. The S70P site shows a difference in glycosylation at N65 (present in our immunogen). S111N, S153A, K155R, K187N, E204N, L275M, K276R, I291A, and R325K are other key differences with our immunogen (labeling with our immunogen first followed by Georgia). These are similar areas to where we believe our immunogen is targeted. Areas of difference with other equine influenzas from the Florida lineage (e.g. Sydney/6085/07) were also identified. Thus, there are key differences in equine HA that may influence how the host responds. Thus, our immunogen may be superior to other equine HAs.

Example 15: Immunogenicity and Protective Efficacy in Ferrets

We next vaccinated ferrets with H3N8, rHA, H3N2 HK/14, or PBS sham by intramuscular vaccination. H3N2 HK/14 was chosen as a direct control for the H3 HA in our H3N8 vaccine but also because it was a recent seasonal vaccine strain. We next examined HAI titers after a single, dual, or tertiary vaccination and found increasing levels of cross-reactive HAI against H1N1 California/09. We then challenged the ferrets three weeks after the tertiary vaccination with H1N1 California/09. Ferrets vaccinated with sham or H3N2 HK/14 has significant lung consolidation. Ferrets vaccinated with rHA form H3N8 had mixed histopathology with areas of clearance and areas with some lung infiltration and consolidation that still appears better than controls. Ferrets vaccinated with H3N8 had lung histology that looked very similar to uninfected controls. Viral burdens were performed by qRT-PCR and we found that H3N8 vaccinated ferrets had the least viral burdens followed by rHA and then the controls.

Ferrets—Male ferrets, aged 4 weeks of age that were castrated and vaccinated for rabies and canine distemper virus, were purchased from Marshall and housed under ABSLII conditions. Ferrets were vaccinated thrice with 50 µl of H3N8, rH3 from H3N8, or H3N2 Hong Kong/2014 containing 25 µg HA and 0.2 µg of Alum in PBS per intramuscular injection. Another group was vaccinated with Alum alone in PBS. Ferrets were then infected intranasally with human influenza strain H1N1 California pnd09 ($10^7$ $TCID_{50}$) in 1 ml of PBS under isofluorane gas.

What is claimed is:

1. A cross-protective influenza vaccine comprising an equine H3 antigen or immunogenic fragment thereof, wherein the equine H3 antigen comprises an amino acid sequence having at least 95% sequence identity to SEQ ID NO: 2 and at least one glycosylated residue; and an adjuvant; wherein the vaccine is cross-protective against two or more subtypes of influenza.

2. The vaccine of claim 1, wherein the equine H3 antigen comprises an amino acid sequence having at least 97% sequence identity to SEQ ID NO: 2.

3. The vaccine of claim 1, wherein the H3 antigen is on the surface of a virus-like particle (VLP) or in secreted form.

4. The vaccine of claim 1, wherein the vaccine is a whole inactivated virus, split viral vaccine, or live attenuated influenza vaccine.

5. The vaccine of claim 1, wherein the vaccine is formulated for delivery via intranasal, intramuscular, subcutaneous, transdermal or sublingual administration.

6. The vaccine of claim 1, wherein said adjuvant is Alum.

7. A cell comprising an equine H3 antigen or immunogenic fragment thereof, wherein the equine H3 antigen comprises an amino acid sequence having at least 95% sequence identity to SEQ ID NO: 2 and at least one glycosylated residue, and wherein the cell is an insect cell or a yeast cell.

8. A method of vaccinating a subject for influenza comprising administering the cross-protective influenza vaccine of claim 1 to a subject in need thereof by intranasal, intramuscular, subcutaneous, transdermal, or sublingual administration.

9. The method of claim 8, further comprising administering to the subject a composition comprising an influenza virus-like particle (VLP) vaccine, a whole inactivated virus, split viral vaccine, or live attenuated influenza vaccine.

10. The method of claim 9, wherein the composition comprising influenza virus-like particle (VLP) vaccine, a whole inactivated virus, split viral vaccine, or live attenuated influenza vaccine is administered before or after the cross-protective influenza vaccine.

11. The method of claim 8, wherein the cross-protective influenza vaccine is administered prior to influenza seasonal vaccination or after influenza seasonal vaccination.

12. The method of claim 11, wherein the period between cross-protective influenza vaccine and seasonal vaccination administration is one day to 10 years.

13. A pharmaceutical composition comprising a synthetic or recombinant equine H3 polypeptide comprising multiple copies of a plurality of influenza virus peptide epitopes, wherein the equine H3 polypeptide comprises an amino acid sequence having at least 95% sequence identity to SEQ ID NO: 2 and at least one glycosylated residue, and at least one seasonal or pandemic preparation against influenza, and containing a pharmaceutically acceptable adjuvant.

14. A method for inducing an immune response or conferring protection against influenza in a subject, wherein the method comprises administering to the subject a pharmaceutical composition according to claim 13.

15. An immunogenic composition comprising an effective amount of a recombinant or synthesized equine H3 antigen or immunogenic fragment thereof, wherein the equine H3 antigen comprises an amino acid sequence having at least 95% sequence identity to SEQ ID NO: 2 and at least one glycosylated residue; an adjuvant; and a pharmaceutically acceptable carrier.

16. A method for generating an immune response to two or more influenza hemagglutinin subtypes and/or influenza types, comprising administering to a subject an effective amount of the immunogenic composition of claim 15, thereby generating the immune response.

17. The method of claim 16, wherein said subject is a mammal.

18. The method of claim 16, wherein said mammal is a human.

19. The method of claim 16, wherein said mammal is a porcine.

\* \* \* \* \*